United States Patent
Kanner et al.

(10) Patent No.: US 7,322,999 B2
(45) Date of Patent: Jan. 29, 2008

(54) TISSUE PUNCH AND METHOD FOR CREATING AN ANASTOMOSIS FOR LOCATING A BYPASS GRAFT

(75) Inventors: Rowland W. Kanner, Guntersville, AL (US); Richard M. Davis, Guntersville, AL (US)

(73) Assignee: Atrion Medical Products, Inc., Arab, AL (US)

( * ) Notice: Subject to any disclaimer, the term of this patent is extended or adjusted under 35 U.S.C. 154(b) by 775 days.

(21) Appl. No.: 10/760,762

(22) Filed: Jan. 20, 2004

(65) Prior Publication Data

US 2004/0225313 A1 Nov. 11, 2004

Related U.S. Application Data

(60) Provisional application No. 60/469,161, filed on May 9, 2003.

(51) Int. Cl.
*A61B 17/34* (2006.01)

(52) U.S. Cl. ...................................................... 606/185

(58) Field of Classification Search ................ 606/151, 606/157, 158, 159, 170, 174, 180, 184, 185; 604/22, 186, 264
See application file for complete search history.

(56) References Cited

U.S. PATENT DOCUMENTS

| | | | |
|---|---|---|---|
| 1,867,624 A | 7/1932 | Hoffman | |
| 3,701,352 A | 10/1972 | Bosworth | |
| 4,018,228 A | 4/1977 | Goosen | |
| 4,216,776 A | 8/1980 | Downie et al. | |
| 4,723,546 A | 2/1988 | Zagorski | |
| 5,129,913 A | 7/1992 | Ruppert | |
| 5,192,294 A | 3/1993 | Blake, III | |
| 5,403,338 A | 4/1995 | Milo | |
| 5,488,958 A | 2/1996 | Topel et al. | |
| D372,310 S | 7/1996 | Hartnett | |
| 5,591,186 A * | 1/1997 | Wurster et al. | 606/185 |
| 5,690,662 A | 11/1997 | Chiu et al. | |
| 5,702,412 A | 12/1997 | Popov et al. | |
| 5,827,316 A | 10/1998 | Young et al. | |

(Continued)

FOREIGN PATENT DOCUMENTS

WO WO 02/074188 9/2002

OTHER PUBLICATIONS

European search report dated Sep. 20, 2004 which issued in connection with corresponding European Application No. 04075754.4.

*Primary Examiner*—Kevin T. Truong
(74) *Attorney, Agent, or Firm*—Trexler, Bushnell, Giangiorgi, Blackstone & Marr, Ltd.

(57) ABSTRACT

A tissue punch which is configured to operate by utilizing a spring force to compress tissue between a rotatable cutter blade and a tissue piercing element. The tissue punch is configured such that once the spring force is applied, the cutter blade can be selectively rotated by the user. The rotation of the blade, assisted by the compression from the spring force, causes the cutter blade to cut through the tissue. Three different methods for creating an anastomosis for locating a bypass graft are disclosed. In each method, bypass graft material is installed on a tissue punch and then sutured. Depending on the method, the tissue is punched either before or after the suturing.

21 Claims, 21 Drawing Sheets

U.S. PATENT DOCUMENTS

| | | |
|---|---|---|
| 5,928,264 A | 7/1999 | Sugarbaker et al. |
| 6,068,637 A | 5/2000 | Popov et al. |
| 6,080,173 A * | 6/2000 | Williamson et al. ........ 606/184 |
| 6,416,527 B1 | 7/2002 | Berg et al. |

* cited by examiner

TISSUE PUNCH AND METHOD FOR CREATING AN ANASTOMOSIS FOR LOCATING A BYPASS GRAFT

RELATED APPLICATION (PRIORITY CLAIM)

This application claims the benefit of U.S. Provisional Application Ser. No. 60/469,161, filed May 9, 2003, which is hereby incorporated herein by reference in its entirety.

BACKGROUND OF THE INVENTION

The present invention generally relates to tissue punches, such as aortic punches used during heart surgery, and more specifically relates to a tissue punch which is configured to use a spring force to compress tissue and then a rotation movement to effect a cut of the tissue.

Another aspect of the present invention generally relates to methods for creating an anastomosis for locating a bypass graft, and more specifically relates to methods which provide that bypass graft material is installed on a tissue punch and then sutured. Depending on the specific method performed, the tissue is cut either before or after the suturing.

Often the goal of heart surgery is to produce blood flow paths around the diseased areas of coronary arteries. To provide as such, saphenous vein grafts are used wherein an opening is formed in the wall of an ascending aorta, then a proximal end of a saphenous vein is anastomosed thereto. To form the opening in the wall of the aorta, an incision can be made using surgical scalpels and/or scissors. Then, an aortic punch can be used in order to attempt to obtain a clean, accurate somewhat larger opening in the aortic wall. Obtaining a clean and accurate opening is extremely important since an opening which is not formed cleanly and accurately often is frayed (albeit microscopically). As a result, the connection of the proximal end of the saphenous vein thereto may not be as reliable, and complications during or after surgery may result. Additionally, rough cut holes as the bypass ostium serve as points for calcification or occlusions. Because heart surgery necessarily often entails the difference between life and death of the patient, it is extremely important to maximize the probability of success of every aspect of the surgical procedure. To this end, it is desirable to try to obtain as clean and as accurate an opening as possible in the wall of the aorta before grafting the saphenous vein thereto.

As mentioned, in attempting to obtain as accurate an opening as possible in the wall of the aorta, surgeons often utilize an aortic punch to form the opening. Typically, the aortic punch will include an anvil, or other support, which is first inserted into the aorta through a small incision in the wall. Then, the surgeon takes his or her hand and approximates the thumb and opposed first and second fingers to push a thumb button while pulling a cross-bar. Consequently, a cutting tube of the aortic punch extends, and slides past, the anvil, thus shearing a larger opening in the aortic wall. Finally, the anvil and cutting tube of the aortic punch are withdrawn from the incision in the wall of the aorta. Examples of prior art aortic punches and similar devices can be found in the following U.S. Pat. Nos. 1,867,624; 3,701,352; 4,018,228; 4,216,776; 5,129,913; 5,192,294; 5,403,338; 5,690,662; 5,827,316 and U.S. Design Pat. No. D372,310.

Because the aortic punch accomplishes cutting the opening in the wall of the aorta by shearing, and effects this shearing by sliding the cutting tube past the anvil, the cut produced is not always extremely clean and accurate, and some fraying of the aortic wall may result. The quality of cut and occurrence of pinching depends upon the fineness and toughness of tissue encountered as well as the sharpness of punch cutting edges and closeness of running clearances among shearing surfaces. A typical aortic punch can often pinch very thin, tough tissue within the close-running, moving punch components, leading to an incomplete hole cutting operation and jamming of the mechanism. Moreover, because the aortic wall is extremely durable, the surgeon must typically exert considerable hand pressure to successfully manipulate the aortic punch to shear the aortic wall. Because shearing of the aortic wall is performed merely by axially sliding a cutting tube across an anvil, the cutting tube of the aortic punch does not remain sharp for very long. Therefore, the cutting tube must be sharpened often, or must be replaced frequently with a sharper cutting tube. Finally, a typical aortic punch is not configured to provide the surgeon with total tactile control of the cutting process, such as effecting a cut only during the pressing of a button or plunger, but not during release of the button or plunger. It is advantageous to provide that the surgeon has effectively total tactile control over the cutting process.

For at least the foregoing reasons, there is a need for an improved tissue punch which can be used to obtain a very clean and accurate opening in tissue without any fraying, which can be used without having to exercise any excessive hand pressure, which does not jam during operation, which does not require that a cutting tube be sharpened or replaced very frequently and which effectively provides the surgeon with total control of the tissue cutting process.

OBJECTS AND SUMMARY

An object of an embodiment of the present invention is to provide a tissue punch which can be used to obtain a clean and accurate cut of tissue with no fraying.

Another object of an embodiment of the present invention is to provide a tissue punch which can be used without having to apply extensive hand pressure.

Still another object of an embodiment of the present invention is to provide a tissue punch which works in such a manner that a cutter of the tissue punch need not be replaced, or sharpened, as frequently.

Still yet another object of an embodiment of the present invention is to provide a tissue punch which does not tend to pinch very thin, tough tissue within close-running, moving punch components, leading to an incomplete hole cutting operation and jamming of the mechanism.

Still yet another object of an embodiment of the present invention is to provide a tissue punch which is designed such that it can be left in place after completing the anastomosis to stop blood flow until the next step in the bypass procedure.

Still yet another object of an embodiment of the present invention is to provide a tissue punch which is designed such that a bypass graft can be threaded over a tube of the tissue punch.

Briefly, and in accordance with at least one of the foregoing, an embodiment of the present invention provides a tissue punch which is configured to operate by utilizing a spring force to compress tissue between a rotatable cutter blade and a tissue piercing element. The tissue punch is configured such that once the spring force is applied, the cutter blade can be selectively rotated by the user. The rotation of the blade, assisted by the compression from the spring force, causes the cutter blade to cut through the tissue.

Other aspects of the present invention provide methods for creating an anastomosis for locating a bypass graft. Specifically, three different methods are described herein. In each method, bypass graft material is installed on a tissue punch and then sutured to tissue, such as to an aorta. Depending on the method, the tissue is punched either before or after the suturing.

BRIEF DESCRIPTION OF THE DRAWINGS

The organization and manner of the structure and function of the invention, together with further objects and advantages thereof, may be understood by reference to the following description taken in connection with the accompanying drawings, wherein like reference numerals identify like elements, and in which:

FIG. 3 is an enlarged view of a portion of the tissue punch, showing a plunger mechanism at a proximal end of the tissue punch in a locked position, wherein a knob is pushed in;

FIG. 10 is similar to FIG. 7, but shows the plunger pushed in;

FIG. 11 is similar to FIG. 9, but shows more of the tissue punch (i.e., is a view from further away), and shows the plunger more fully pushed in;

DESCRIPTION OF EMBODIMENTS OF THE INVENTION

Figure 1:
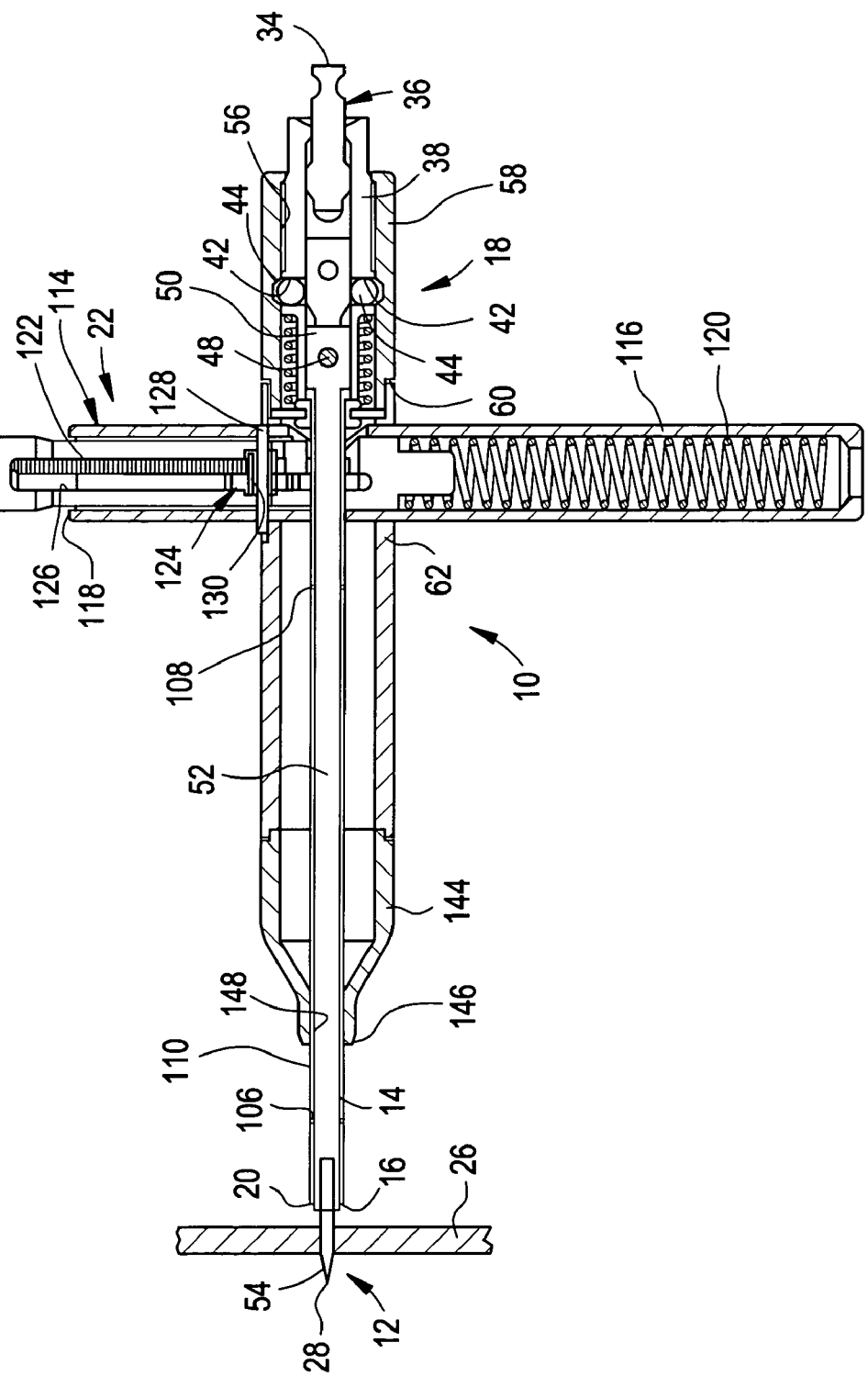
FIG. 1 is a cross-sectional view of a tissue punch which is in accordance with an embodiment of the present invention.

While the present invention may be susceptible to embodiment in different forms, there are shown in the drawings, and herein will be described in detail, embodiments with the understanding that the present description is to be considered an exemplification of the principles of the invention and is not intended to limit the invention to that as illustrated and described herein.

FIG. 1 illustrates, along with the remaining FIGURES, a tissue punch 10 which is in accordance with an embodiment of the present invention. The tissue punch can be used to obtain a clean and accurate cut of tissue with no fraying in the area of the excised tissue, without having to apply extensive hand pressure and without having to frequently replace or sharpen a cutter blade. While the typical operating force required for a standard aortic punch is in the area of 16 to 40 pounds, a tissue punch in accordance with an embodiment of the present invention preferably requires only a few ounces of operating force. Preferably, the tissue punch is designed such that an internal return spring offers more resistance than the tissue being cut. The tissue punch does not tend to pinch very thin, tough tissue within close-running, moving punch components, leading to an incomplete hole cutting operation and jamming of the mechanism. The tissue punch is designed such that it can be left in place after completing the anastomosis to stop blood flow until the next step in the bypass procedure, and is designed such that a bypass graft can be engaged or threaded over a tube of the tissue punch preparatory to grafting to the aorta either prior to or after formation of the anastomosis. The tissue punch can be used in connection with various methods, steps of which are illustrated in FIGS. 18-31, which provide that bypass graft material is installed on the tissue punch and then sutured to tissue. Depending on the specific method performed, the tissue is punched either before or after the suturing.

As shown in FIG. 1, the tissue punch 10 includes a puncturing tip 12 and a cylindrical tube 14 which provides a cutter blade 16 at its end. The tissue punch 10 also includes a first, spring biased, plunger mechanism 18 which is configured to operate in two modes—a first mode where the mechanism maintains the puncturing tip 12 in a position extending from the end 20 of the cylindrical tube 14, and a second mode where the mechanism spring biases the puncturing tip 12 axially into the cylindrical tube 14. The tissue punch 10 of the disclosed embodiment also includes a second plunger mechanism 22 which is selectively operable to rotate the cylindrical tube 14 and the cutter blade 16 affixed at the end 20 thereof to cut away a plug 24 of tissue 26. The plunger mechanisms will be described in more detail later hereinbelow.

Figure 2:
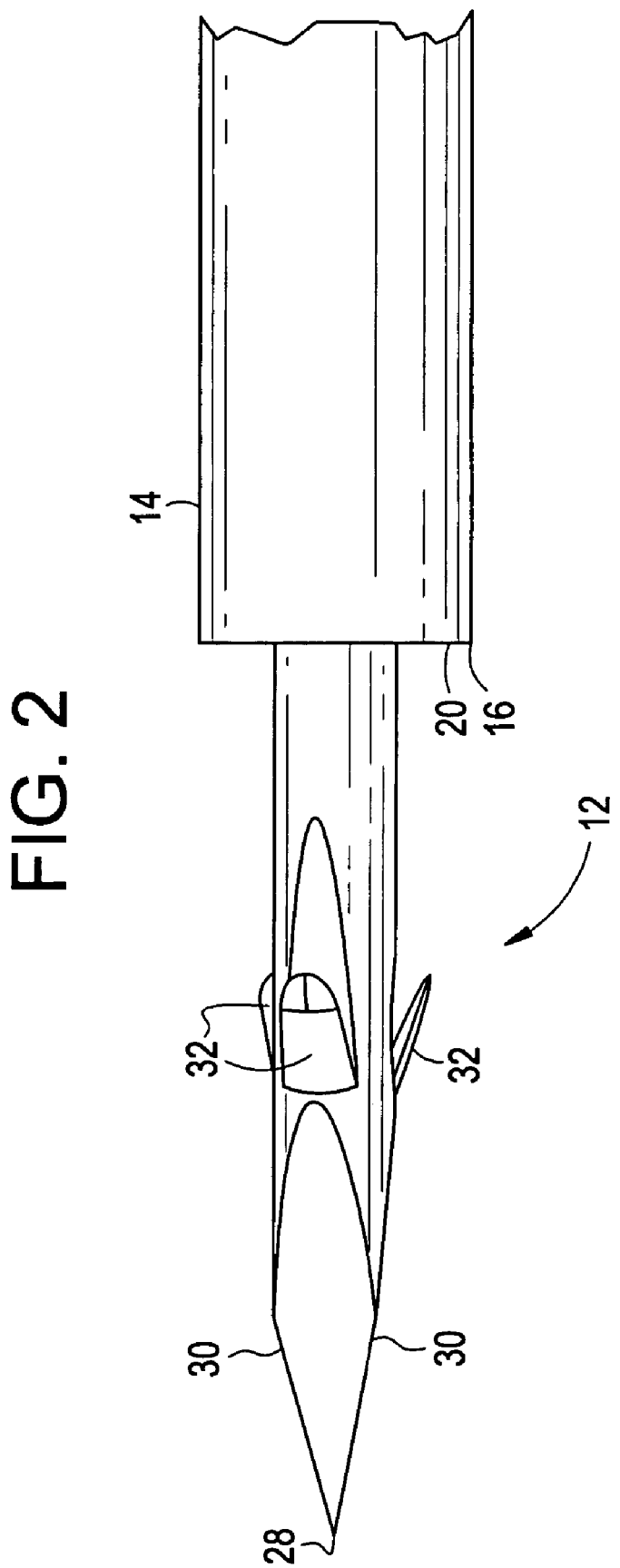
FIG. 2 is a view of a distal end of the tissue punch, showing a puncturing tip extending from a cutter blade.

FIG. 2 illustrates a preferred embodiment of the puncturing tip 12. As shown, the puncturing tip 12 is preferably a trocar-type tip, which includes a sharp, pointed tip 28, and three angled cutting edges 30 (one every 120 degrees around) about the tip 28. The pointed tip 28 and three cutting edges 30 provide that the puncturing tip 12 can pierce tissue 26 with very low force. Preferably, a barb 32 is provided above and between each cutting edge 30, and each barb 32 is relatively sharp. The cutter blade 16 is also preferably provided as being sharp such that as the barbs 32 slide into the end 20 of the cylindrical tube 14, past the cutter blade 16 provided at the end 20 of the cylindrical tube 14, the tissue gets cut. Although a preferred embodiment of the cutter blade 16 is illustrated in FIG. 2, other embodiments are entirely possible. For example, the cutter blade may be serrated.

Although a preferred embodiment of the puncturing tip is shown in FIG. 2, other embodiments are entirely possible. For example, the puncturing tip can be provided as a spiral point and the tissue punch can be configured to rotate the spiral point to cause initial piercing of the tissue.

As will be described more fully later herein, in use, the sharp point 28 is pierced into tissue 26 (see FIGS. 1, 6, and 11), such as into an aorta. As explained more fully hereinafter, thereafter the plunger end 36 is released so that a spring force stored in the tissue punch 10 is released, causing the barbs 32 to compress the tissue 26 between the barbs and the cutter blade 16. Then, the cutter blade 16 is rotated, causing the cutter blade 16 to cut through the tissue, and causing a plug 24 to be cut out of the tissue 26 and pulled into the cylindrical tube 14 (see FIGS. 12-14). The sharp tip 28 facilitates easy puncturing of tissue 26, such as that of an aorta, when pressed against same. The barbs 32 provide that once the puncturing tip 12 is inserted into tissue 26, the tip 12 cannot be easily pulled out of the tissue 26. As shown in FIG. 2, the barbs 32 are preferably curved generally upward, toward a proximal end 34 of the tissue punch 10, such that as the barbs 32 retract into the end 20 of the rotating cutter blade 16, cutting a plug 24 out of the tissue 26 (see FIGS. 12-14), they tend to retain the plug 24 on the puncturing tip 12. In other words, in use, the barbs 32 function as tissue retaining members. Although a preferred embodiment of the barbs 32 is shown in FIG. 2, other configurations can be used.

Figure 4:
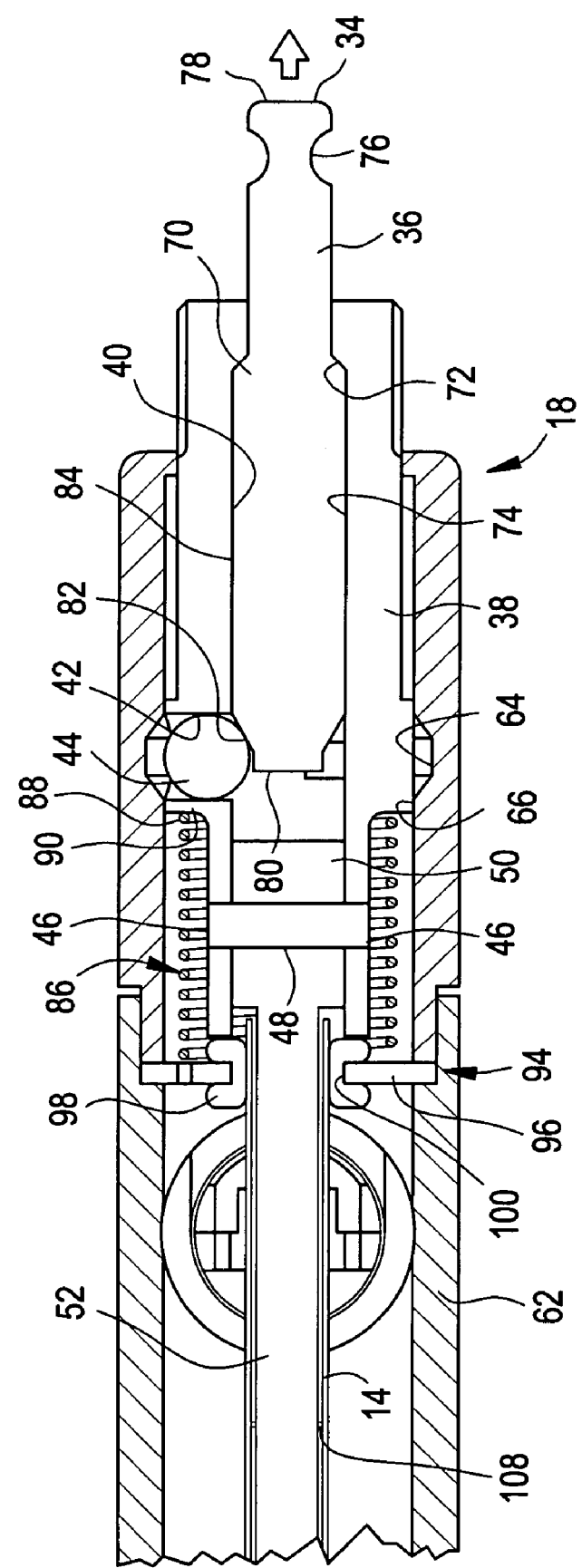
FIG. 4 shows the plunger mechanism at the proximal end of the tissue punch in an unlocked position, wherein the knob is pulled out and a spring has not yet expanded (i.e., the spring remains compressed)
Figure 5:
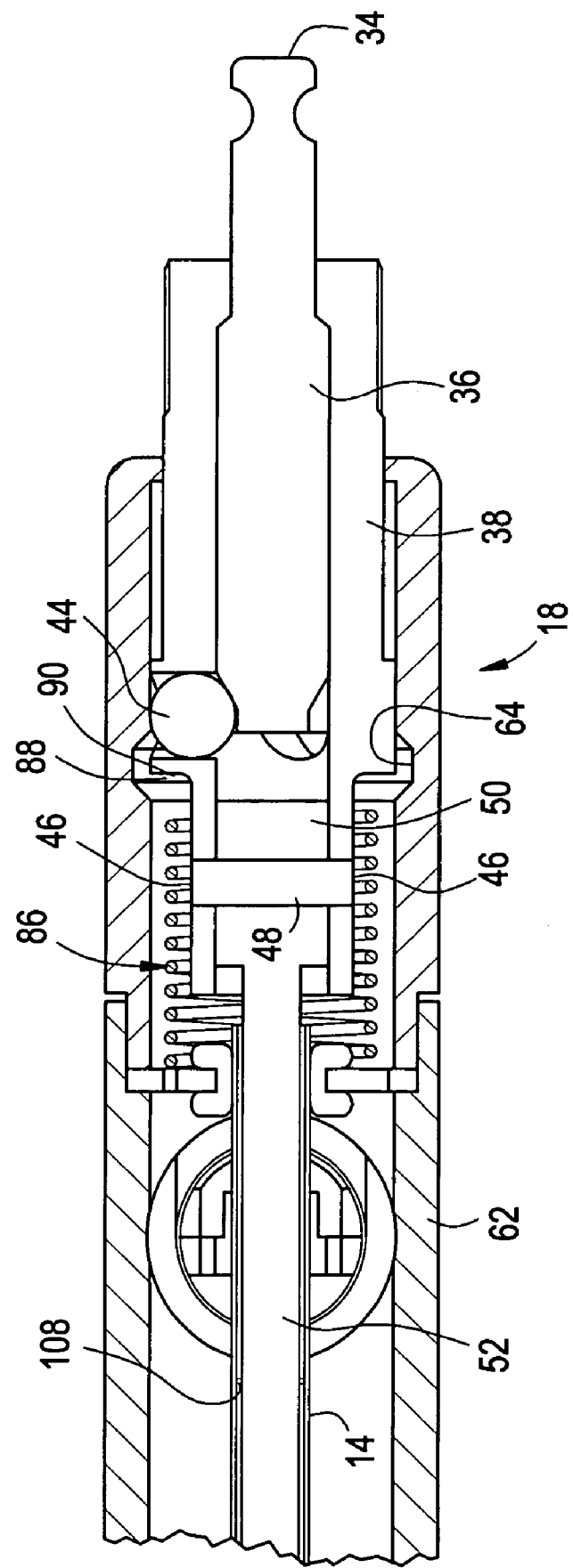
FIG. 5 is similar to FIG. 4, but shows the plunger mechanism after the spring has expanded.

As discussed briefly above, the first, spring biased, plunger mechanism 18 is configured to operate in two modes—a first mode where the mechanism maintains the puncturing tip 12 in a position extending from the end 20 of the cylindrical tube 14 (i.e., out from the cutter blade 16), and a second mode where the mechanism spring biases the puncturing tip 12 axially upward into the cylindrical tube 14. As shown in FIGS. 4 and 5, the plunger mechanism 18 includes a knob 36 at the proximal end 34 of the tissue punch 10, and the knob 36 is received in a generally cylindrical member 38 having a longitudinal throughbore 40. The cylindrical member 38 also includes openings 42 for receiving locking balls 44, and a bore 46 for receiving a pin 48 which extends through the end 50 of a shaft-like member 52, thereby securing the cylindrical member 38 to the shaft-like member 52. An opposite end 54 of the shaft-like member 52 provides the puncturing tip 12 (see FIG. 1). The cylindrical member 38 is received in a bore 56 in a housing member 58, and the housing member 58 is secured to the end 60 of a longitudinal, main housing component 62 of the tissue punch 10. The housing 58 is provided with a circumferential recess or detent 64 (see FIGS. 4 and 5) on an internal wall 66 of the housing member 58 for receiving the balls 44.

Figure 3:
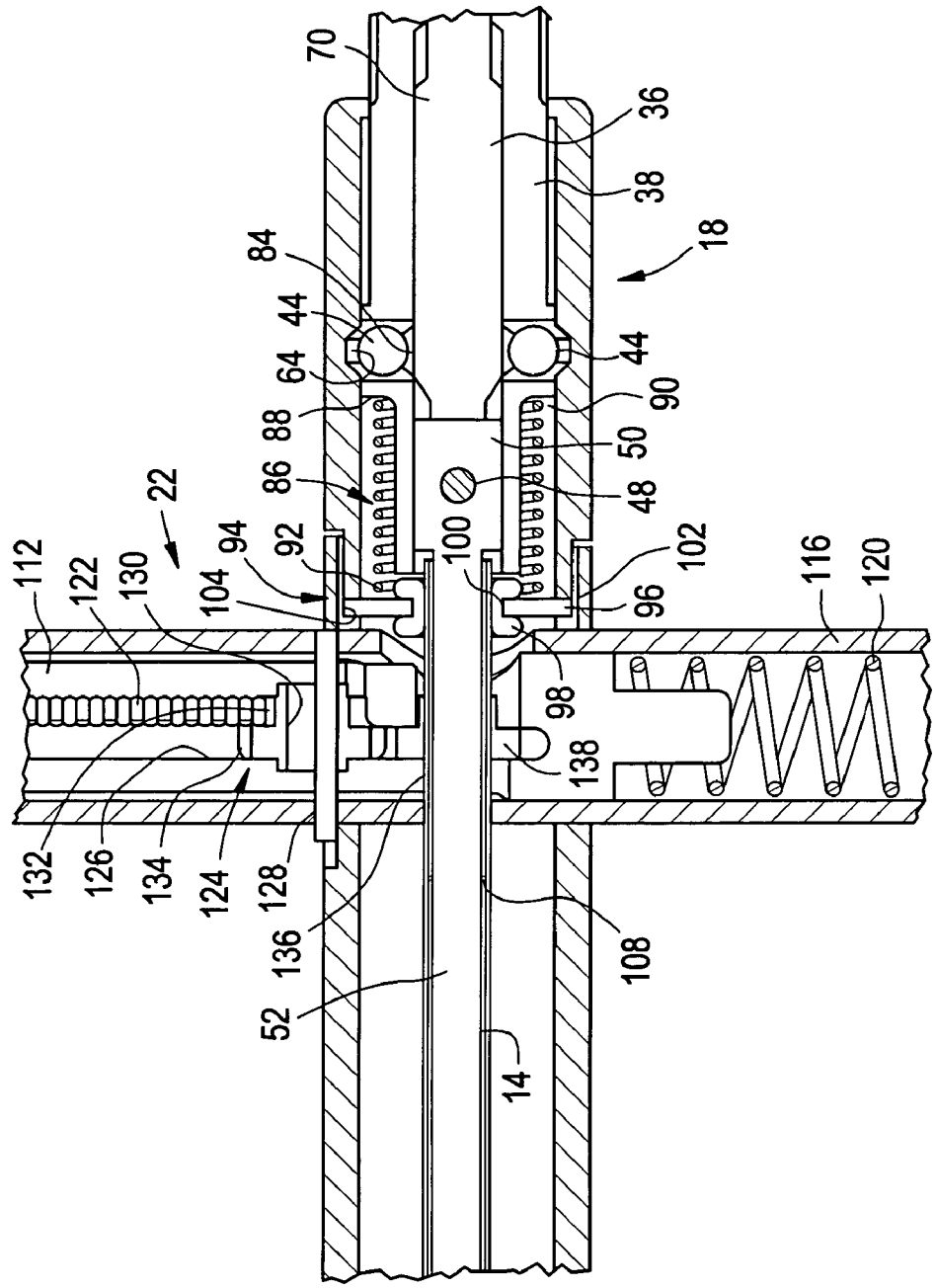

The knob 36 includes a shoulder 70 which tends to prevent the knob 36 from being pulled out (or falling out) of the cylindrical member 38 (see FIG. 4). The cylindrical member 38 includes a corresponding shoulder 72 on an internal surface 74 thereof. As shown, a circumferential indent 76 may be provided proximate an end 78 of the knob 36 to facilitate gripping the knob 36 with ones fingers. An opposite end 80 of the knob 36 provides an inwardly-tapering portion 82 for engaging the balls 44. More specifically, as shown in FIG. 3, when the balls 44 abut wall 84 of the knob 36, the balls 44 tend to be positioned in the internal recess 64 provided in the cylindrical member 38. In contrast, as shown in FIG. 4, when the balls 44 abut the inwardly-tapering end portion 82 of the knob 36, the balls 44 tend be positioned out of the internal recess 64 provided in the housing 58.

As shown in FIG. 4 for example, the plunger mechanism 18 includes a spring 86, and one end 88 of the spring 86 contacts an external shoulder 90 of the cylindrical member 38. Another end 92 of the spring 86 contacts a retaining assembly 94 which includes a retaining washer 96 and bushing 98, where the bushing 98 abuts the cylindrical tube 14 and receives an inside circumferential surface 100 of the retaining washer 96. An outside circumferential surface 102 of the retaining washer 96 is retained in an internal recess 104 provided in the tissue punch 10.

Figure 6:
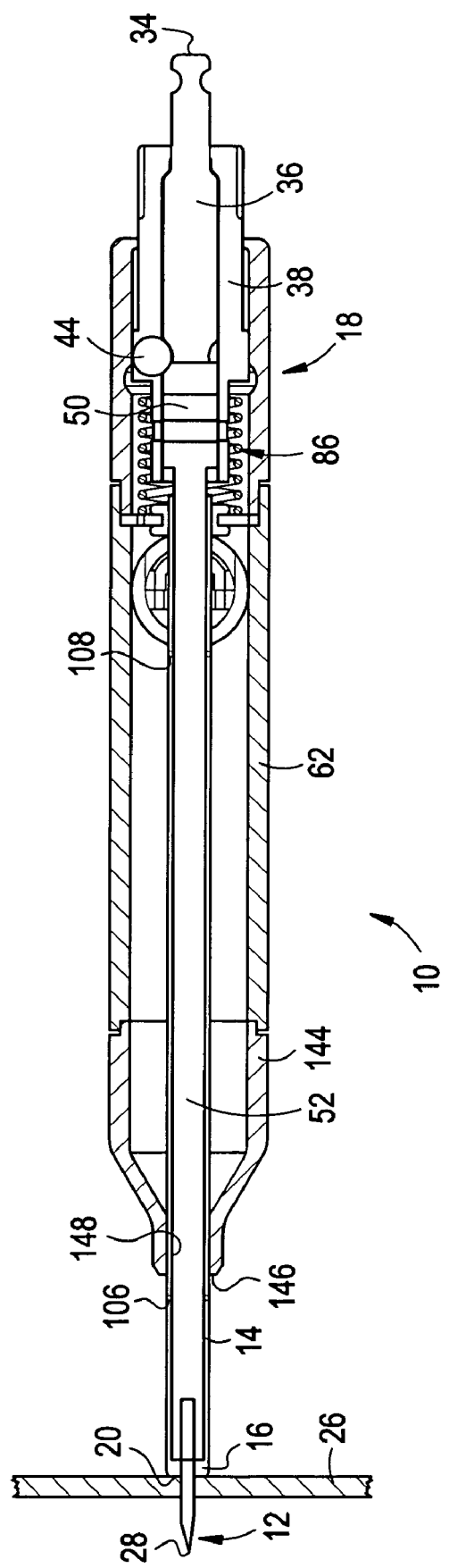
FIG. 6 shows the tissue punch with the plunger mechanism at the proximal end in the unlocked position, wherein the knob is pulled out, the spring is expanded, and the puncturing tip is engaged in a hole in tissue.
Figure 7:
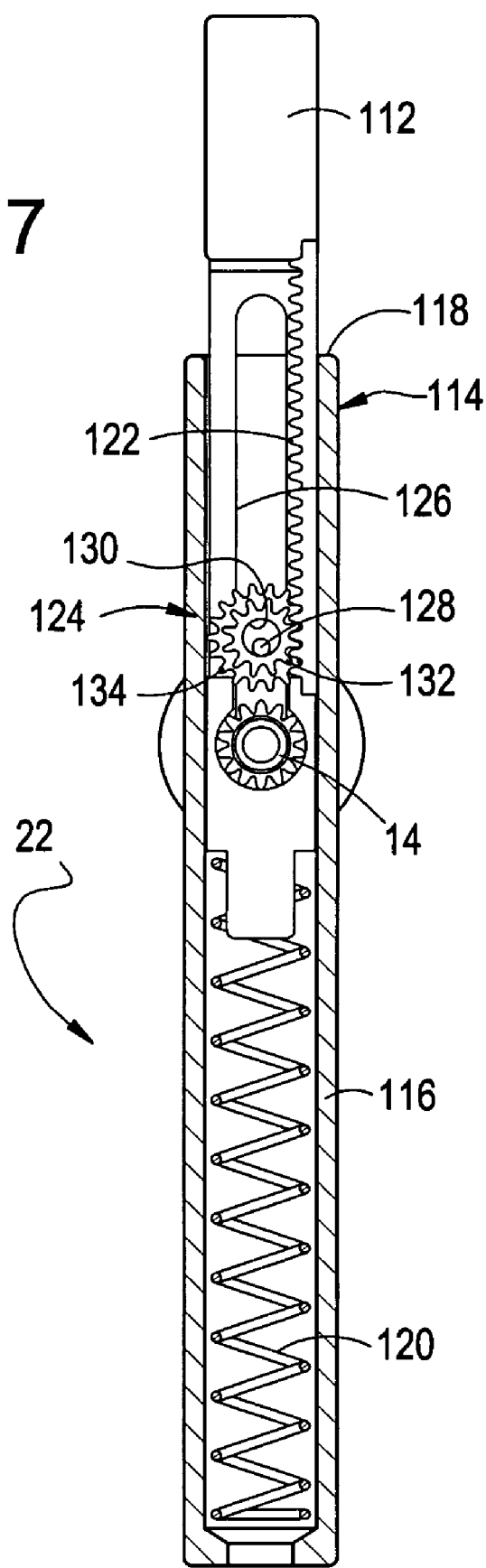
FIG. 7 shows a portion of a second plunger mechanism of the tissue punch, wherein a plunger is not pushed in and a gear set is not engaged with a gear on a cylindrical tube.

As shown in FIG. 3, when the knob 36 is pushed in (i.e., into the cylindrical member 38), the balls 44 fall into the internal recess 64 and secure the cylindrical member 38 in place, with the spring 86 compressed (preferably the spring bias force is less than one pound). As shown in FIGS. 4-6, when the knob 36 is pulled out (i.e., relative to the cylindrical member 38), the balls 44 fall out of the internal recess 64 (into the holes 42 in the side of the cylindrical member 38), allowing the spring 86 to push the cylindrical member 38 toward the proximal end 34 of the tissue punch 10. Because the shaft-like member 52 is pinned to the cylindrical member 38, this causes the end 50 of the shaft-like member 52 to move toward the proximal end 34 of the tissue punch 10. This causes the puncturing tip 12 to retract axially into the cylindrical tube 14 unless the puncturing tip 12 is engaging tissue 26, in which case the tissue is compressed between the barbs 32 on the puncturing tip 12 and the cutter blade 16. Preferably, the characteristics of the spring 86 are selected such that the spring 86 does not tend to have the puncturing tip 12 draw excess tissue into the cylindrical tube 14 just prior to the cutter blade 16 breaking through the tissue, as this can result in a hole that is flared out at the cutter exit rather than remaining cylindrical throughout the length of the hole. Preferably, the spring 86 is selected to provide the desired, generally light spring force.

As shown in FIG. 1, preferably sealing members 106, 108, such as o-rings, are provided on an external surface 110 of the shaft-like member 52, and the sealing members 106, 108 seal with the cylindrical tube 14 and generally prevent blood or other contaminants from traveling into the cylindrical tube 14 and into contact with internal components of the tissue punch 10.

Figure 17:
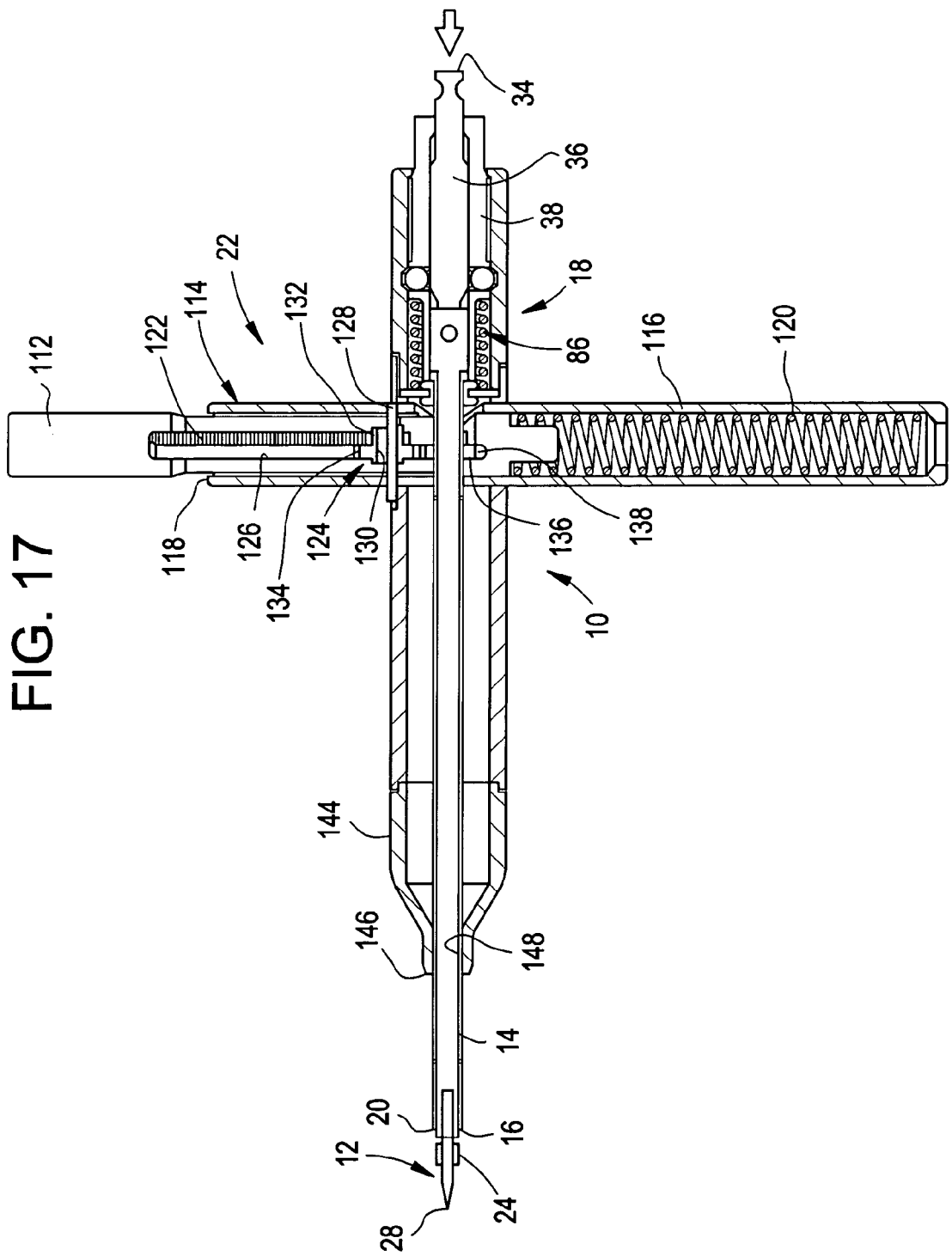
FIG. 17 is similar to FIG. 16, but shows the knob at the proximal end pushed in, thereby extending the puncturing tip from the cutter blade to expose the tissue plug.

As discussed and as shown in FIGS. 3 and 17, when the knob 36 is pushed in, the balls 44 fall into the internal recess 64 and secure the cylindrical member 38 in place. At this time, the puncturing tip 12 is locked in position, extending from the end 20 of the cylindrical tube 14 (i.e., extending from the end 20 of the cutter blade 16). In such a state, the tissue punch 10 is prepared for piercing the puncturing tip 12 into tissue 26, such as an aorta. Subsequently, the knob 36 is pulled out, as shown in FIGS. 4-6 and 11, causing the balls 44 to fall out of the recess 64 in the tissue punch 10, thereby allowing the spring 86 to push the cylindrical member 38 toward the proximal end 34 of the tissue punch 10. This causes the puncturing tip 12 to tend to retract into the cylindrical tube 14, causing the barbs 32 on the puncturing tip 12 to contact the tissue 26 in preparation of a cutting operation which is effected by actuating the second plunger mechanism 22.

While one embodiment of the plunger mechanism 18 is disclosed, still other alternative embodiments are entirely possible. For example, a locking mechanism similar to that which is employed in connection with a conventional ball point pen can be used, or a simple catch and release latching mechanism can be used. Still other embodiments are entirely possible.

Figure 11:
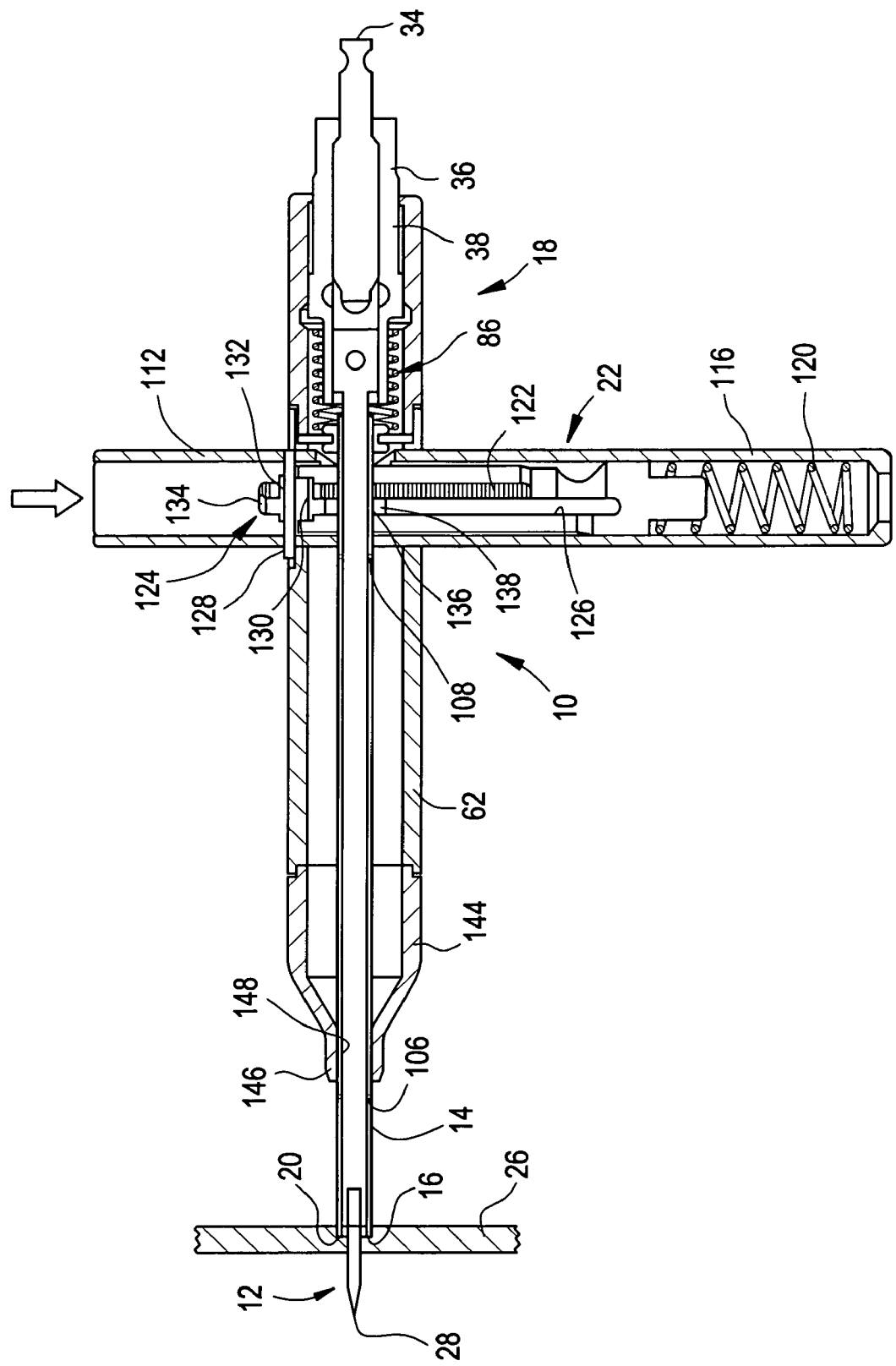

As discussed briefly above, the second plunger mechanism 22 is configured to rotate the cylindrical tube 14 and therefore the cutter blade 16 on the distal end thereof. More specifically, the second plunger mechanism 22 is configured such that a user can actuate the mechanism using his or her finger and cause the cutter blade 16 to rotate, preferably at least one revolution every time the plunger mechanism 22 is fully actuated. As shown in FIG. 11, preferably the plunger mechanism 22 is configured such that it includes a button or plunger 112 which can be pushed by a user, and that the pushing causes the cutter blade 16 to rotate at least one revolution as the plunger 112 is fully pushed in, but does not cause the cutter blade 16 to rotate as the plunger 112 is released. The plunger 112 is pushable along a first axis, causing the cutter blade 16 to rotate about a second axis, wherein the first axis and the second axis are transverse, preferably perpendicular, to each other. If the plunger 112 is only partially pushed in, the cutter blade 16 rotates only a portion of total amount of revolutions. As such, the plunger mechanism 22 is configured to provide that a user, i.e., surgeon, has, effectively, complete control over the cutting operation. Additionally, this provides that single direction tension is maintained on the tissue under the cutter blade 16 during the cut to create a smooth edge, to minimize trauma to adjacent tissue and to avoid wasted cutter blade rotational motion due to tissue elasticity. With the tissue punch described herein, very little incidental tissue damage can occur beyond the cut edge.

Figure 8:
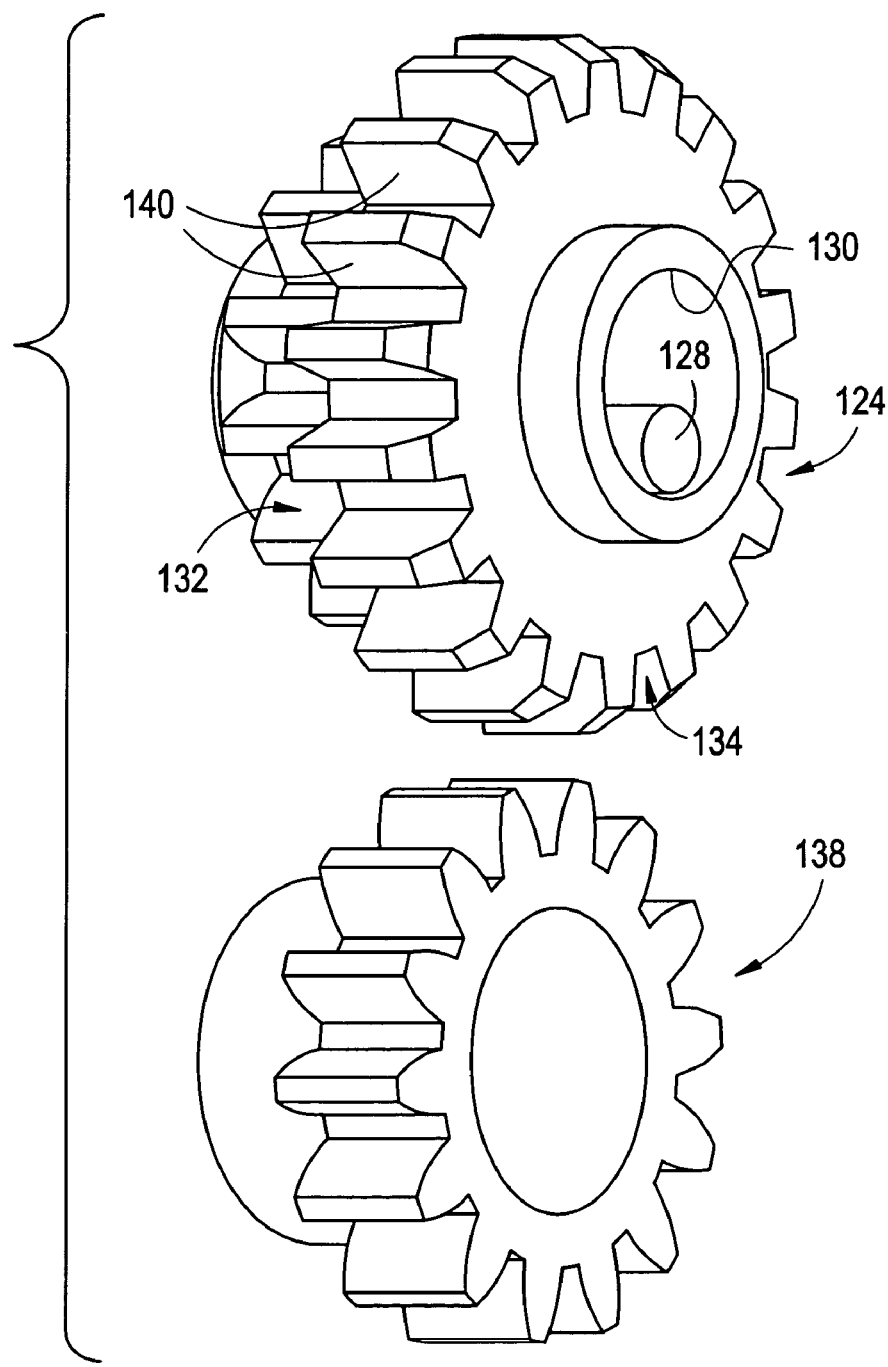
FIG. 8 shows the gears of FIG. 7 isolated and disengaged.
Figure 9:
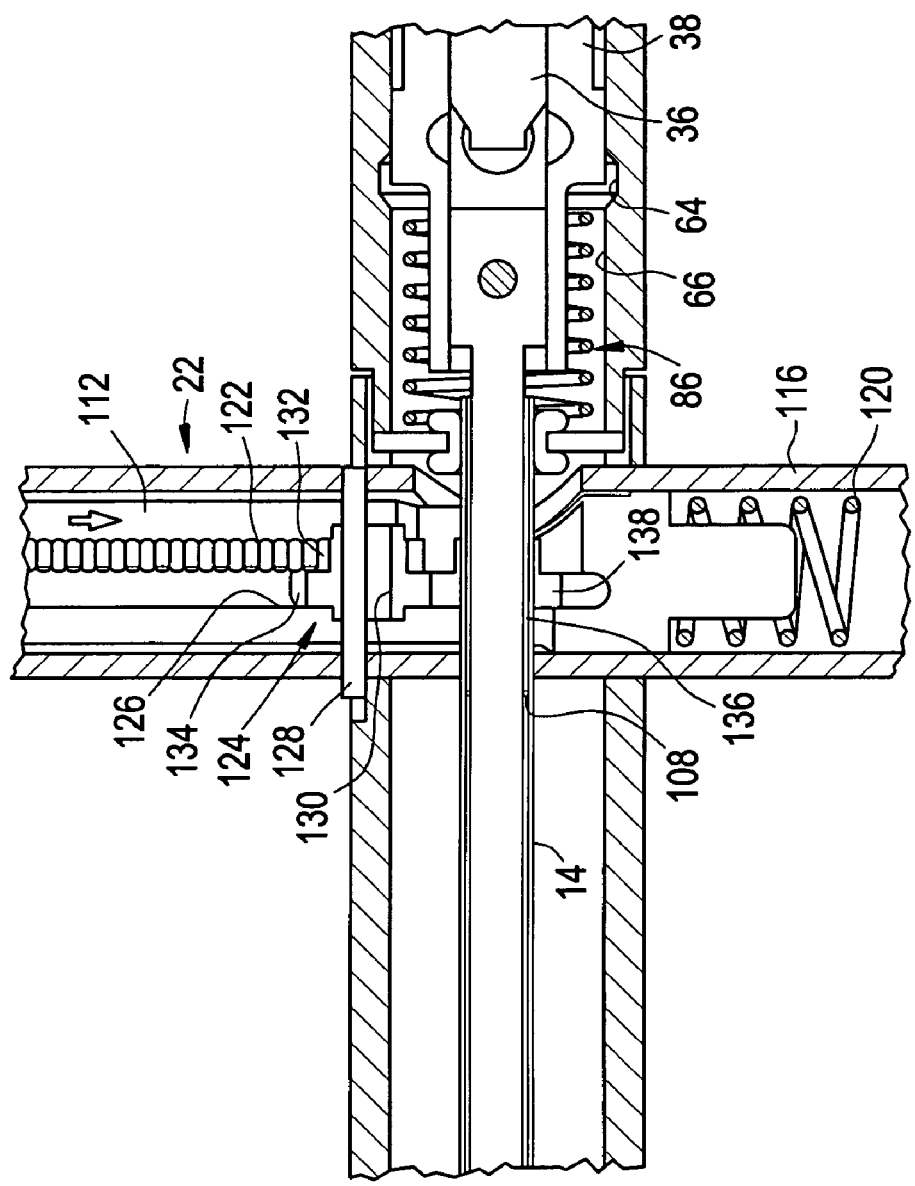
FIG. 9 shows a portion of the tissue punch, and shows the gears of FIG. 7 engaged with each other.
Figure 10:
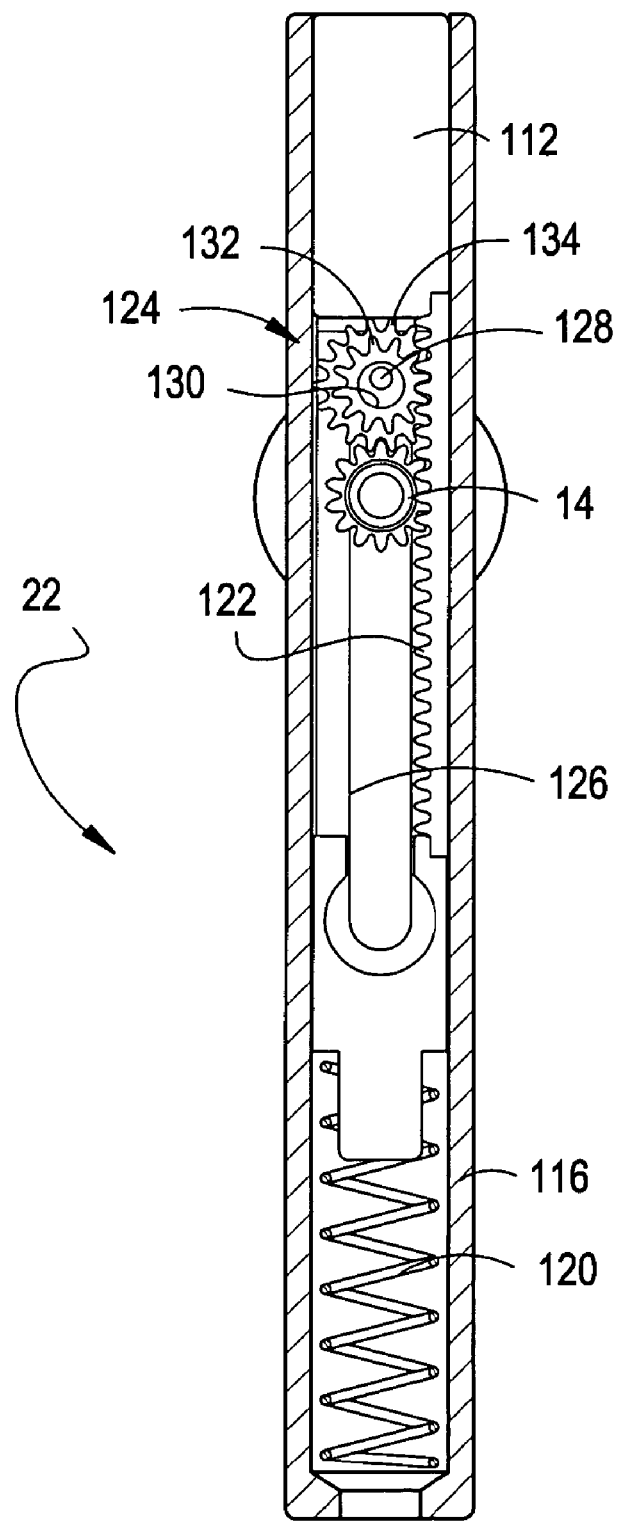
Figure 14:
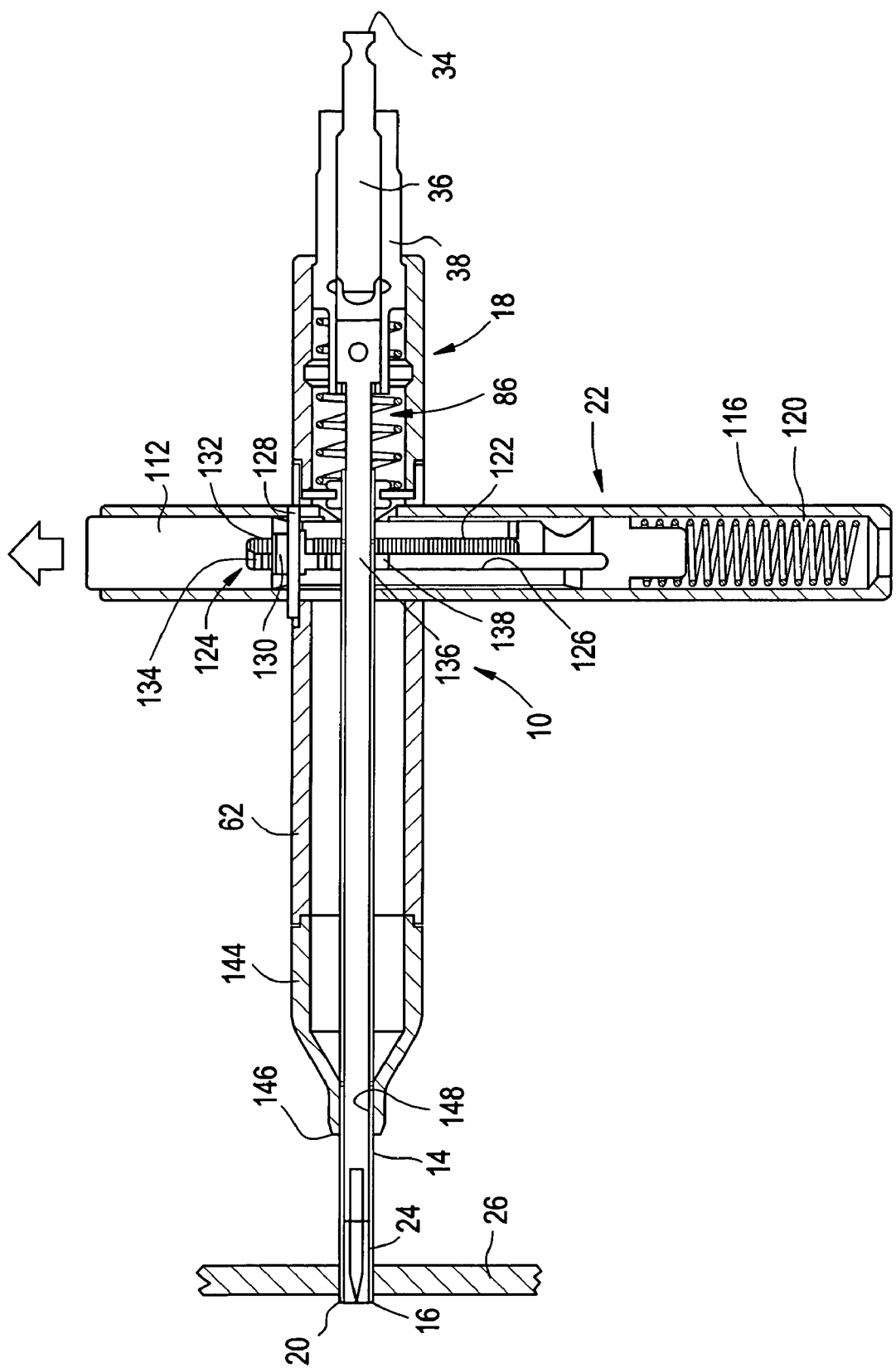
FIG. 14 is similar to FIGS. 11 and 12, but shows the plunger being released and the gear set being disengaged.
Figure 15:
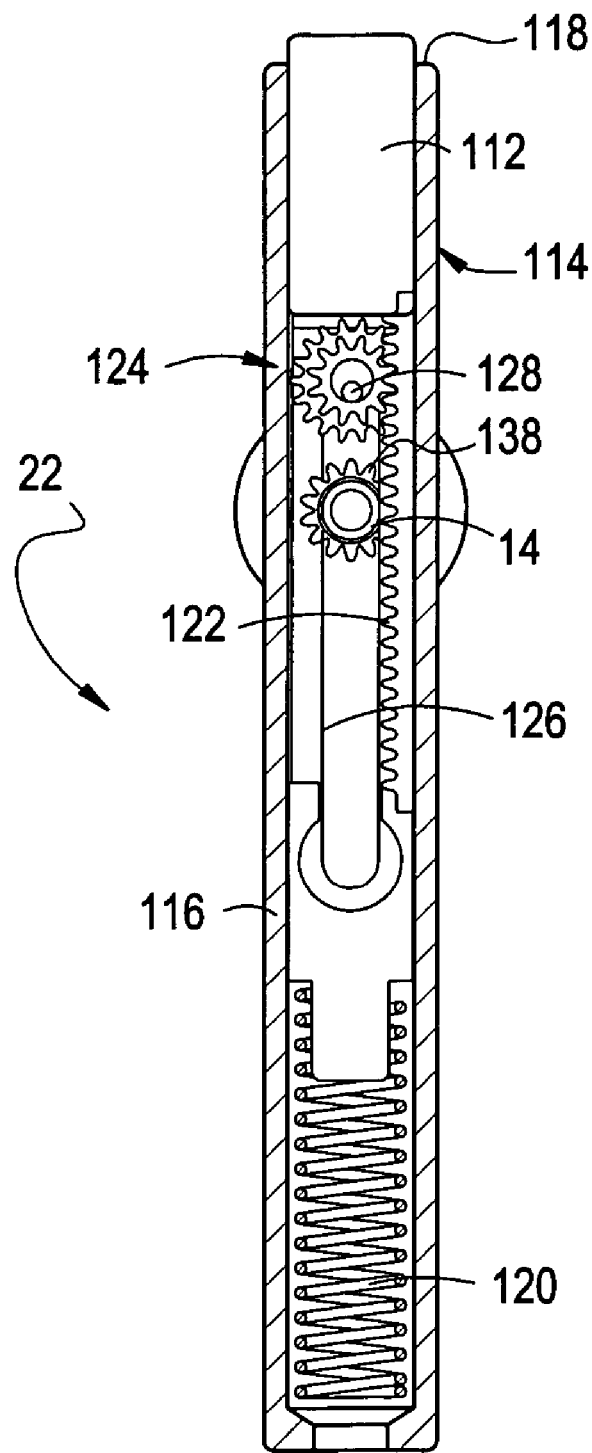
FIG. 15 is similar to FIG. 10, but shows the gears disengaged.
Figure 16:
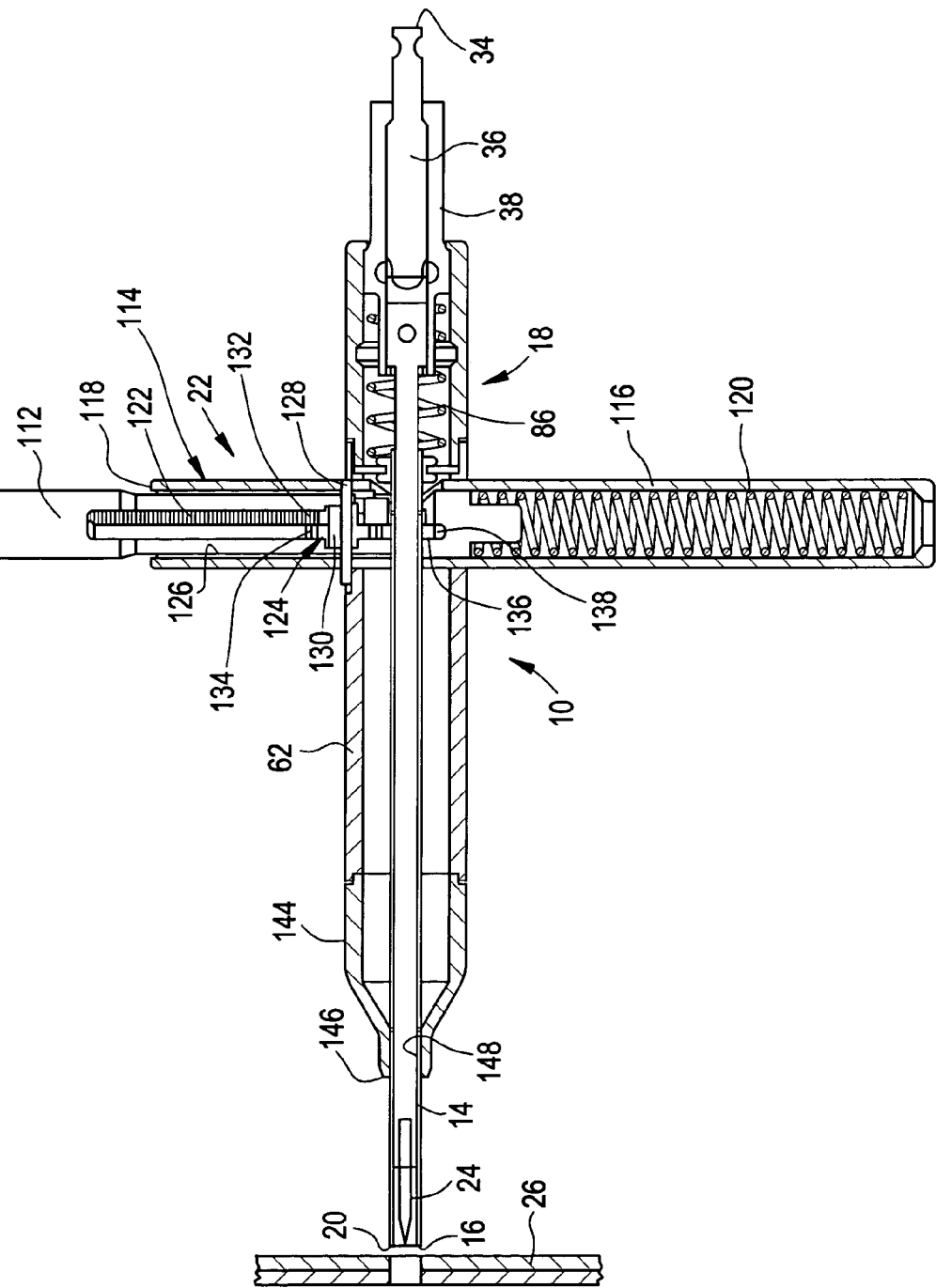
FIG. 16 shows the tissue punch with the plunger fully released, and a plug of tissue having been cut out by the tissue punch and retained in the cylindrical tube.

As shown in FIGS. 1, 3, 7, 9, 10-12 and 14-17, the plunger mechanism 22 includes a housing component 114 which includes a bore 116 extending in one end 118 thereof. A spring 120 is retained in the housing 114, and the spring 120 biases the plunger 112 out of the bore 116. The plunger 112 includes a rack 122, and an intermediate, free-floating gear set 124 is provided and is free to traverse within a slot 126 positioned parallel to the rack 122. The free-floating gear set 124 is retained by a pin 128 which is mounted in the housing 114, and extends through a bore 130 in the gear set 124 (see FIG. 8). The pin 128 has a smaller cross-sectional diameter that does the bore 130 in the gear set 124. Hence, the pin 128 has play in the bore 130 to provide a lost-motion type of connection. The gear set 124 is a compound gear which consists of a small pinion 132 mounted with common axis to a larger gear 134 preferably having more teeth. When the small pinion 132 of the gear set 124 is engaged with the rack 122, the small pinion 132 is driven by motion of the rack 122. Mounted to an external surface 136 of the cylindrical tube 14 (or provided as being integral with the cylindrical tube 14) is a corresponding gear 138 which is engageable with the gear teeth 140 on the larger gear 134 of the gear set 124, such that when the small pinion 132 of the gear set 124 is engaged with the rack 122, the small pinion 132 as well as the cylindrical tube 14 are driven by motion of the rack 122. Initially, as shown in FIG. 9, as the rack 122 is driven inward by compressing the plunger 112, the gear set 124 is displaced longitudinally within the slot 126 and driven into engagement with the gear 138 which is attached to the cylindrical tube 14. Thereafter, as shown in FIG. 11, further pressing of the plunger 122 causes the rack 122 to advance further which causes the cutter blade 16 to rotate. As shown in FIG. 14, releasing the plunger 112 to return to its starting point immediately withdraws the intermediate gear set 124 away from the gear 138 on the cylindrical tube 14, thus releasing the cylindrical tube 14 from control by the rack 122, and allowing the tube 14 to freewheel.

The gear set 124 is limited in fore and aft travel by the pin 128 which is mounted in the housing 114 and extends through the bore 130 in the gear set 124. This travel limiting feature can be effected using different structure. For example, a fixed pin (i.e., a pin which has a cross-sectional diameter which is substantially the same as the bore in the gear set, such that the pin cannot substantially play in the bore) could be provided with the gear set, and external stops could be positioned in the housing to arrest motion of the gear set in both the fore and aft travel directions. Alternatively, the gear set 124 can be provided with an integral axle which interacts with stops in the housing.

While the second plunger mechanism 22 is described as being a rack and pinion type mechanism, other mechanical linkage mechanisms can be used. For example, a capstan can be provided as being driven with a string-like member wrapped around the capstan, or another mechanism can be used. For example, the tissue punch can be configured such that initial actuation of the plunger mechanism which rotates the cutter blade causes the tissue punch to exert a biasing or spring force on the puncturing tip (i.e., without having to pull out the pin at the proximal end of the tissue punch). Still further, the plunger mechanism 22 can be provided as being a gear arrangement which is driven by a direct drive motor (i.e. electric, hydraulic, pneumatic) and, for example, a remote controller can be used to operate the mechanism.

As discussed above, the plunger mechanism 22 can be configured to effect two revolutions of the cutter blade 16 every time the plunger 112 is pushed. Alternatively, the plunger mechanism 22 can be configured to effect either more or less than two revolutions for every actuation of the plunger mechanism 22. The number of revolutions effected by each push of the plunger 112 can be set by selecting a certain gear ratio between gears 134 and 138 which causes the desired number of revolutions upon each push of the plunger 112.

As shown in FIG. 1, the tissue punch 10 further includes an end housing piece 144 which is secured or otherwise engaged with housing piece 62. The end housing piece 144 tapers generally inward at its end 146, thereby providing an internal surface 148 which is in rubbing contact with the cylindrical tube 14.

In use, initially the knob 36 is pushed in as shown in FIGS. 1 and 3, causing the puncturing tip 12 to be locked in position, extending from the end 20 of the cylindrical tube 14 (i.e., extending from the end 20 of the cutter blade 16). Then, the puncturing tip 12 is pierced into tissue 26, such as an aorta. Then, the knob 36 is pulled out as shown in FIGS. 4-6, causing the balls 44 to fall out of the recess 64 in the tissue punch 10, thereby allowing the spring 86 to push the cylindrical member 36 toward the proximal end 34 of the tissue punch 10. This causes the puncturing tip 12 to tend to retract into the cylindrical tube 14, causing the barbs 32 on the puncturing tip 12 to contact the tissue 26 as shown in FIG. 6. Thereafter, a tissue plug cutting operation is effected by actuating the second plunger mechanism 22.

Figure 12:
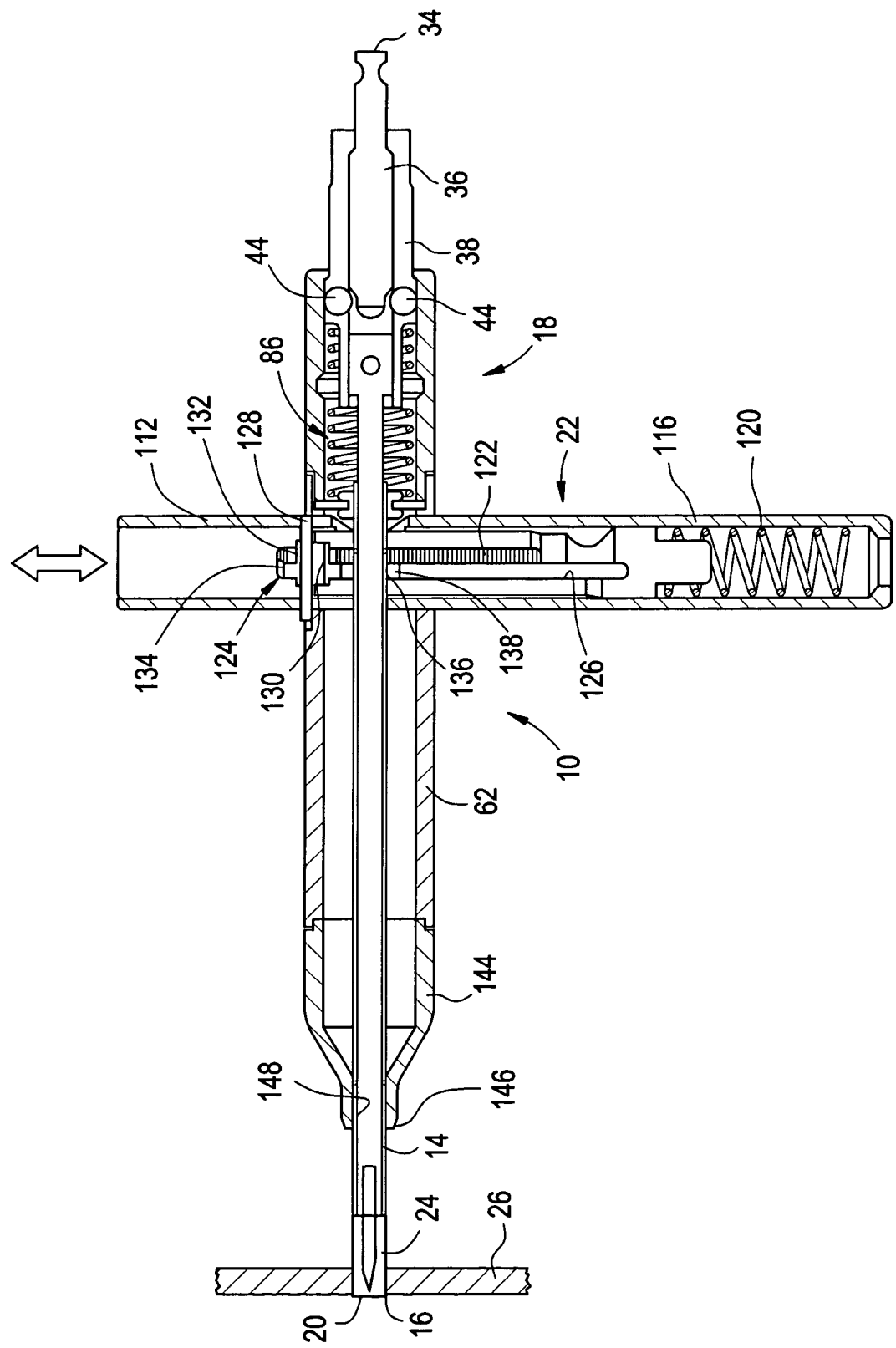
FIG. 12 is similar to FIG. 11, but shows the spring at the proximal end of the tissue punch expanded.
Figure 13:
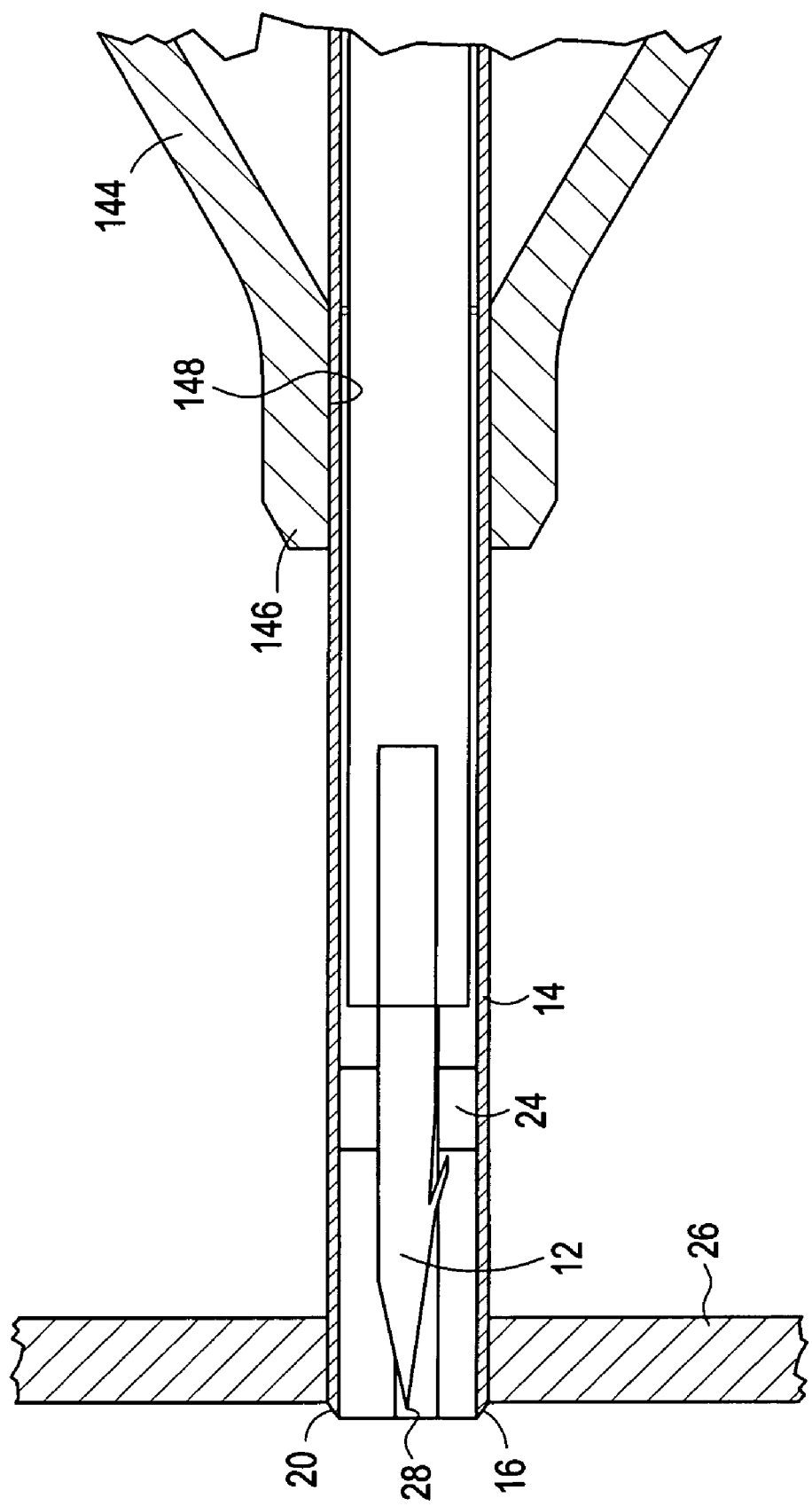
FIG. 13 is similar to FIG. 12, but provides an enlarged view of the puncturing tip and the plug of tissue.

Specifically, as shown in FIGS. 9 and 11, the plunger 112 is pushed using a finger, and if the plunger 112 is pushed all the way in, this causes the cutter blade 16 to rotate two revolutions, causing the cutter blade 16 (in cooperation with the barbs 32 on the puncturing tip 12) to cut a plug 24 out of the tissue 26 as shown in FIGS. 12 and 13. Specifically, as shown in FIG. 9, when the plunger 112 is initially pressed in, the rack 122 is driven inward, and the gear set 124 is displaced longitudinally within the slot 126 and driven into engagement with the gear 138 which is attached to the cylindrical tube 14. Thereafter, as shown in FIG. 11, further pressing of the plunger 112 causes the rack 122 to advance further which causes the cutter blade 16 to rotate. As shown in FIG. 14, releasing the plunger 112 to return to its starting point immediately withdraws the intermediate gear set 124 away from the gear 134 on the cylindrical tube 14, thus releasing the cylindrical tube 14 from control by the rack 122, and allowing the tube 14 to freewheel. As the cutter blade 16 rotates, the plunger mechanism 18 at the proximal end 34 of the tissue punch 10 (specifically the spring 86 of the plunger mechanism 18) maintains a pulling force on the puncturing tip 12. Therefore, as the cutter blade 16 rotates, the barbs 32 on the puncturing tip 12 pull on the tissue 26. As shown in FIGS. 12-14, as a plug 24 is cut out of the tissue 26, the barbs 32 retain the plug 24 on the puncturing tip 12 and pull the plug 24 into the cylindrical tube 14. Thereafter, the knob 36 can be pushed in as shown in FIG. 17, (causing the balls 44 to lock in place in the recess 64), causing the puncturing tip 12 to lock in place, extending from the cutter blade 16, at which time the plug 24 can be removed from the puncturing tip 12.

The tissue punch 10 disclosed herein can be used to obtain a clean and accurate cut of tissue with no fraying, without having to apply extensive hand pressure and without having to frequently replace or sharpen a cutter blade. The tissue punch does not rely on traditional shearing or scissoring action of two close-running metal edges, so the tissue punch does not tend to jam up with or pinch very fine tissue. Instead, it operates by utilizing a pre-determined spring force to compress tissue between the rotating cutter blade 16 and the barbs 32. Once this spring force is applied, the sharp cutter blade 16 is caused to rotate (i.e., selectively by the user). The rotation of the cutter blade 16, assisted by the compression from spring force, allows the cutter blade 16 to cut through the tissue. Although specific embodiments of the spring biased mechanism 18 and the cutter blade rotating mechanism 22 are described, other embodiments are entirely possible while still retaining the inventive concept of the present invention.

Figure 18:
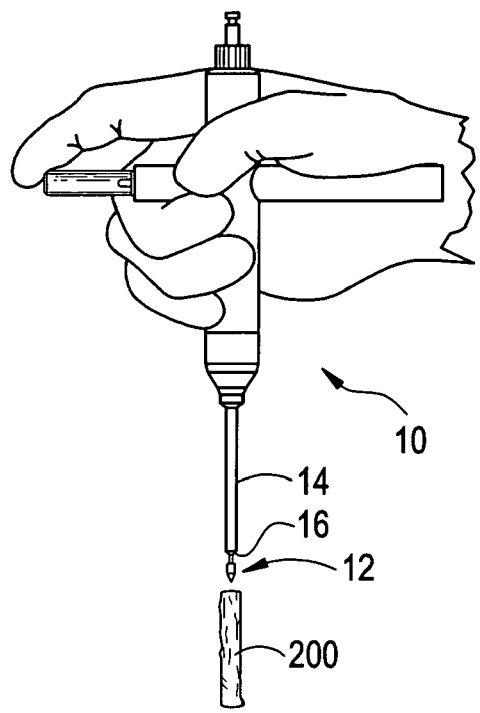
FIGS. 18-31 show various steps of methods which are in accordance with various embodiments of the present invention.
Figure 19:
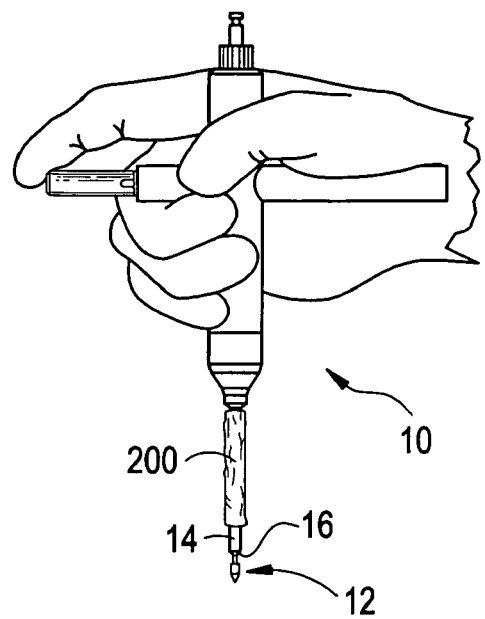
Figure 20:
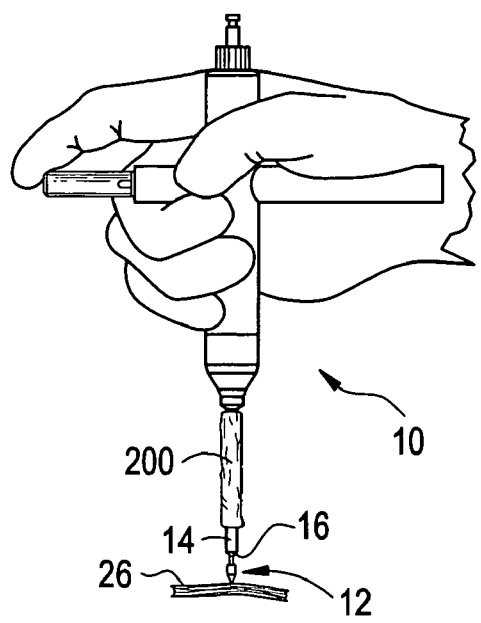
Figure 21:
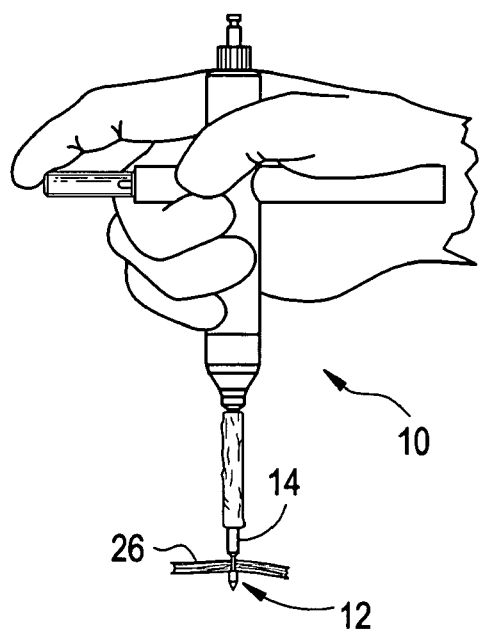
Figure 22:
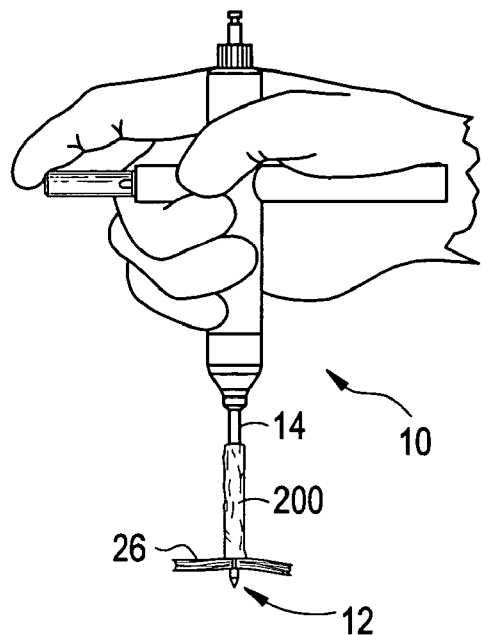
Figure 23:
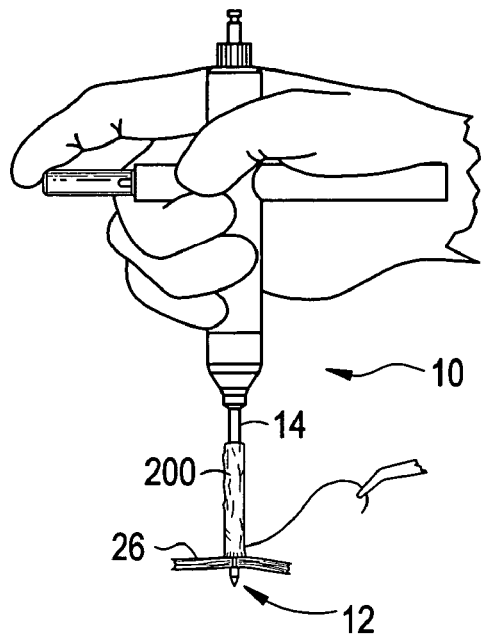
Figure 24:
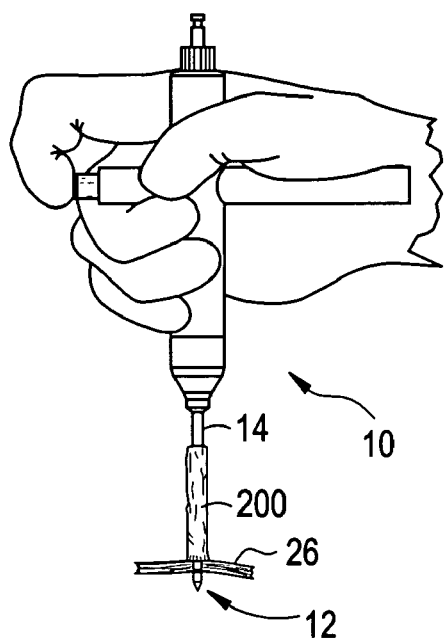
Figure 25:
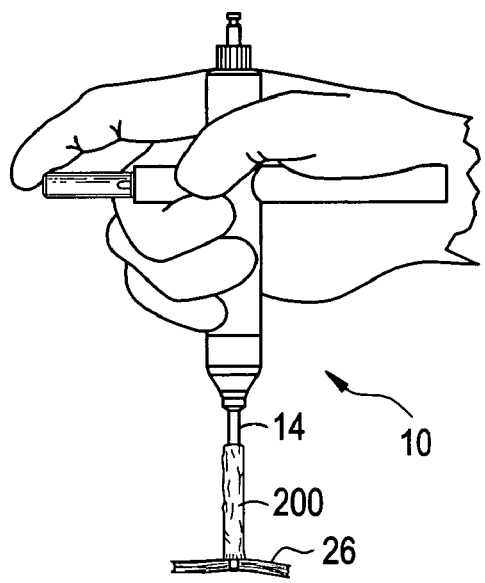
Figure 26:
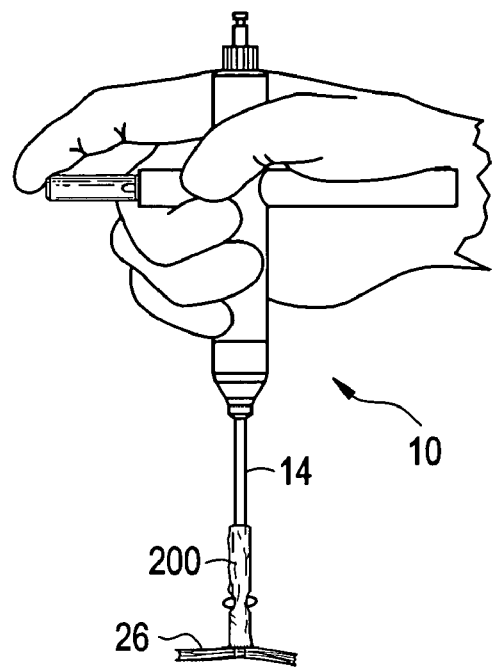

The design of the tissue punch makes possible several different methods for creating an anastomosis and for locating and effecting a bypass graft. Three methods are disclosed herein and illustrated generally in FIGS. 18-31. Specifically, a first method provides that a bypass graft material 200 is installed upon the cylindrical tube 14 as shown in FIGS. 18 and 19 prior to engagement of the device with the aorta. Then, the puncturing tip 12 is pressed against the tissue 26 as shown in FIG. 20 (i.e., while the knob 36 of the tissue punch 10 is pushed in), such as to an aorta wall, causing the tip 12 to puncture the tissue 26 as shown in FIG. 21. The knob 26 of the tissue punch 10 is pulled out to release the spring load and compress tissue between the barbs 32 of the puncturing tip 12 and the cutter blade 16. Thereafter, as shown in FIG. 22, the graft material 200 is slid down the cylindrical tube 14 to contact the tissue 26, such as the aorta wall. As shown in FIG. 23 the graft material 200 is next sutured to the tissue 26, and the plunger mechanism 22 is actuated as shown in FIG. 24 (see also FIG. 10), causing the cutter blade 16 to rotate until ostium is created and anastomosis is created. The tissue punch 10 is partially withdrawn from the graft material 200 as shown in FIG. 25 and the graft material 200 is clamped as shown in FIG. 26 to maintain hemostasis, prior to completely removing the tissue punch 10 from the graft. Finally, the knob 36 of the tissue punch 10 is pressed in to expose the plug 24 for removal from the tissue punch 10 (see also FIG. 17).

Figure 27:
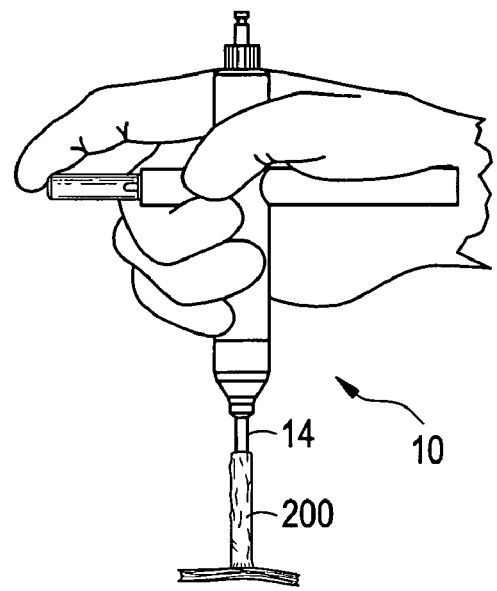
Figure 28:
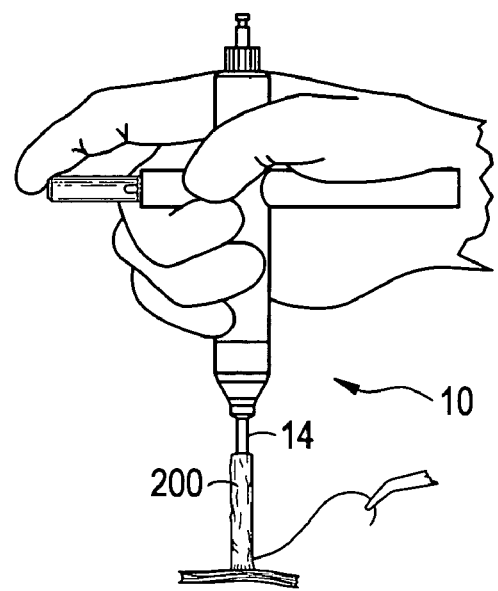
Figure 29:
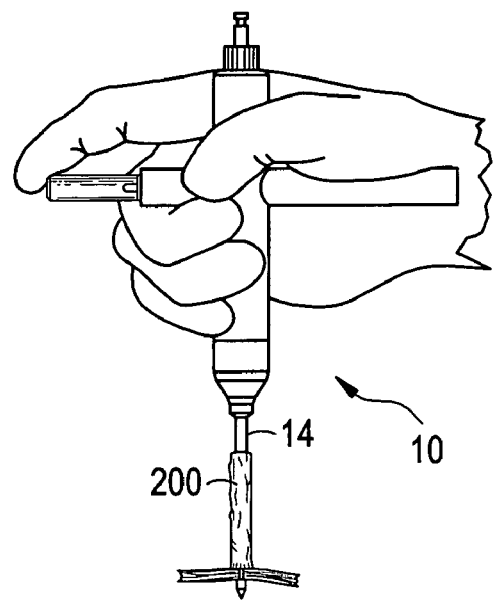

A second method is similar to the first method and also provides that the bypass graft material 200 is installed upon the cylindrical tube 14 (see FIGS. 18 and 19) prior to engagement with the tissue 26. The puncturing tip 12 is presented to the tissue 26 (see FIG. 20) (i.e., while the knob 36 of the tissue punch 10 is pushed in). Then, the graft material 200 is slid down the cylindrical tube 14 to contact the tissue 26, such as the aorta wall as shown in FIG. 27. The graft material 200 is now sutured to the tissue 26 as shown in FIG. 28, and the tissue punch 10 is pushed to cause the puncturing tip 12 to puncture the tissue 26 as shown in FIG. 29. Following puncturing, the knob 36 of the tissue punch 10 is pulled out to release the spring load and compress tissue between the barbs 32 of the puncturing tip 12 and the cutter blade 16. The plunger mechanism 22 is next actuated, as shown in FIG. 24 (see also FIG. 10), causing the cutter blade 16 to rotate until ostium is created and anastomosis is created. The tissue punch 10 is partially withdrawn from the graft material 200, as shown in FIG. 25, and the graft material 200 is clamped as shown in FIG. 26 to maintain hemostasis, prior to completely removing the tissue punch 10 from the graft 200. Finally, the knob 36 of the tissue punch 10 is pressed in to expose the plug 24 for removal from the tissue punch 10 (see also FIG. 17).

Figure 30:
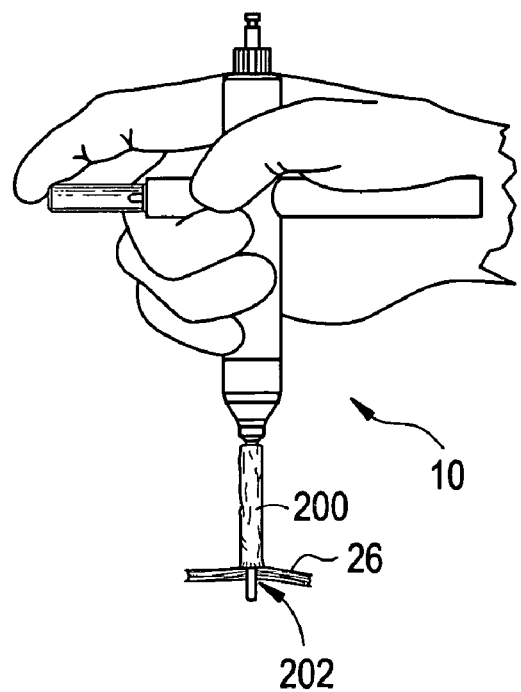
Figure 31:
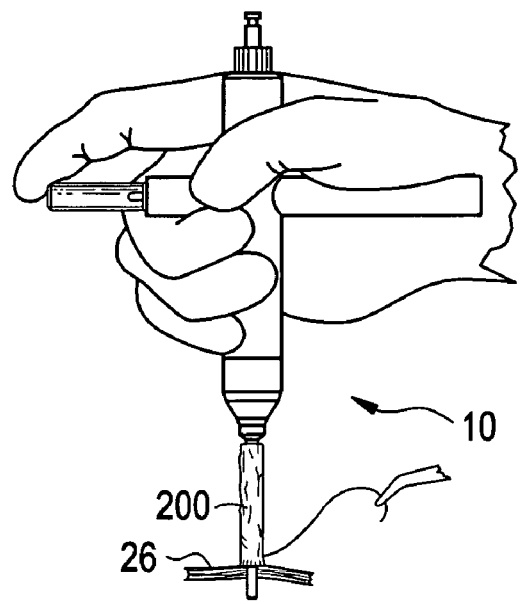

A third method is similar to the first two methods, and also provides that a bypass graft material 200 is installed upon the cylindrical tube 14 (see FIGS. 18 and 19). The puncturing tip 12 element is pressed against tissue 26, such as an aorta wall as shown in FIG. 20 (i.e., while the knob 36 of the tissue punch 10 is pushed in), causing the puncturing tip 12 to puncture the tissue 26 as shown in FIG. 21. As shown in FIG. 22, the graft material 200 is next moved down the cylindrical tube 14 to contact the tissue 26, such as the aorta wall. Then, the knob 36 of the tissue punch 10 is pulled out to release the spring load and compress tissue between the barbs 32 of the puncturing tip 12 and the cutter blade 16. Thereafter, the plunger mechanism 22 is actuated as shown in FIG. 24 (see also FIG. 10), causing the cutter blade 16 to rotate until ostium and anastomosis are created. Then, as shown in FIG. 30, the cutter blade 16 is maintained in the hole 202 in the tissue 26 to provide hemostasis and position graft 200 to tissue 26 (i.e., aorta). As shown in FIG. 31, the graft material 200 is now sutured to the tissue 26, the tissue punch 10 is then partially withdrawn from the graft material 200 as shown in FIG. 25, and the graft material 200 is clamped to maintain hemostasis as shown in FIG. 26, prior to completely removing the tissue punch 10 from the graft 200. Finally, the knob 36 of the tissue punch 10 is pressed in to expose the plug 24 for removal from the tissue punch 10 (see also FIG. 17).

The tissue punch disclosed herein facilitates the anastomosis process by allowing bypass material (harvested donor vessel or rayon) to be installed upon the cylindrical tube before the ostium is created. The cutter blade also serves to promote hemostasis since it can be left in the punctured hole as a plug against blood flow until the anastomosis is completed. This is important in "beating heart" bypass procedures.

While several embodiments of the present invention are shown and described herein, it is envisioned that those skilled in the art may devise various modifications and equivalents without departing from the spirit and scope of the invention. For example, the puncturing tip 12 can be provided as a spiral, piercing tip and the tissue punch (i.e., the plunger mechanism at the proximal end) could be configured to rotate the spiral, piercing tip to cause the tip to initially pierce the tissue. Furthermore, the cutter blade 16 could be provided as a serrated-type blade. Still further, the tissue punch can be configured such that initial actuation of the plunger mechanism 22 which rotates the cutter blade causes the tissue punch to exert a biasing or spring force on the puncturing tip (i.e., without having to pull out the knob at the proximal end). Because modifications such as these are possible without departing from the spirit and scope of the present invention, the present invention is not intended to be limited by the foregoing disclosure.

What is claimed is:

1. A tissue punch for cutting a hole in tissue, said tissue punch comprising: a cylindrical tube having a cutter blade at its end; and a plunger movable to rotate the cylindrical tube, wherein said cylindrical tube has a cutter blade at its end, said tissue punch further comprising a shaft-like member disposed in the cylindrical tube, having a sharp tip at its end for piercing tissue, and having tissue-retaining structure proximate the tip, said tissue punch configured to pierce a hole in the tissue using the sharp tip, compress tissue between the tissue-retaining structure and the cutter blade, cut away tissue using rotation of the cutter blade and application of a spring biased force on the shaft-like member, and retain the cut away tissue using the tissue-retaining structure proximate the sharp tip.

2. A tissue punch as recited in claim 1, wherein the first axis and the second axis are perpendicular to each other.

3. A tissue punch as recited in claim 1, wherein the sharp tip comprises a plurality of angled cutting edges.

4. A tissue punch as recited in claim 3, wherein the tissue-retaining structure comprises a plurality of sharp barbs provided above and between the angled cutting edges.

5. A tissue punch as recited in claim 1, further comprising a spring biasing mechanism engageable with the shaft-like member, said tissue punch configured such that said tissue-retaining structure is extendable from the cutter blade against force of the spring biasing mechanism.

6. A tissue punch as recited in claim 1, further comprising a knob at an end of the tissue punch, said knob being received in a generally cylindrical member.

7. A tissue punch as recited in claim 6, said first plunger mechanism further comprising balls, a pin and a shaft-like member having an end, said cylindrical member including openings for receiving the balls and two holes for receiving said pin, said pin extending through the end of the shaft-like member, thereby securing the cylindrical member to the shaft-like member, wherein an opposite end of the shaft-like member provides a puncturing tip.

8. A tissue punch as recited in claim 7, said tissue punch further comprising a housing component having an end, said first plunger mechanism further comprising a housing member having a bore, said cylindrical member being received in the bore in said housing member, and the housing member being secured to the end of said housing component.

9. A tissue punch as recited in claim 7, wherein said cylindrical member includes a circumferential recess for receiving the balls.

10. A tissue punch as recited in claim 7, wherein an end of the knob provides an inwardly-tapering portion for engaging the balls, wherein when the balls abut a wall of the knob, the balls tend to be positioned in the internal recess provided in the cylindrical member, and when the balls abut the inwardly-tapering portion of the knob, the balls tend to be positioned out of the internal recess provided in the cylindrical member.

11. A tissue punch as recited in claim 6, wherein said cylindrical member includes an internal shoulder which tends to prevent the knob from being pulled out of the cylindrical member, said cylindrical member including a corresponding shoulder on an external surface thereof.

12. A tissue punch as recited in claim 6, wherein said knob has an end, further comprising a circumferential indent proximate the end, thereby facilitating gripping of the knob.

13. A tissue punch as recited in claim 6, said plunger mechanism further comprising a spring and a retaining assembly, one end of the spring contacting an external shoulder of the cylindrical member, another end of the spring contacting the retaining assembly.

14. A tissue punch as recited in claim 13, said retaining assembly comprising a retaining washer and a bushing, wherein the bushing abuts the cylindrical tube and receives an inside circumferential surface of the retaining washer, wherein an outside circumferential surface of the retaining washer is retained in an internal recess provided in the tissue punch.

15. A tissue punch for cutting a hole in tissue, said tissue punch comprising: a cylindrical tube having a cutter blade at its end; and a plunger movable along a first axis to rotate the cylindrical tube about a second axis, said first axis and said second axis being transverse to each other, further comprising a knob at an end of the tissue punch, said knob being received in a generally cylindrical member, said first plunger mechanism further comprising balls, a pin and a shaft-like member having an end, said cylindrical member including openings for receiving the balls and two holes for receiving said pin, said pin extending through the end of the shaft-like member, thereby securing the cylindrical member to the shaft-like member, wherein an opposite end of the shaft-like member provides a puncturing tip.

16. A tissue punch as recited in claim 15, said tissue punch further comprising a housing component having an end, said first plunger mechanism further comprising a housing member having a bore, said cylindrical member being received in the bore in said housing member, and the housing member being secured to the end of said housing component.

17. A tissue punch as recited in claim 15, wherein said cylindrical member includes a circumferential recess for receiving the balls.

18. A tissue punch for cutting a hole in tissue, said tissue punch comprising: a cylindrical tube having a cutter blade at its end; and a plunger movable along a first axis to rotate the cylindrical tube about a second axis, said first axis and said second axis being transverse to each other, further comprising a knob at an end of the tissue punch, said knob being received in a generally cylindrical member, wherein said cylindrical member includes an internal shoulder which tends to prevent the knob from being pulled out of the cylindrical member, said cylindrical member including a corresponding shoulder on an external surface thereof.

19. A tissue punch as recited in claim 15, wherein an end of the knob provides an inwardly-tapering portion for engaging the balls, wherein when the balls abut a wall of the knob, the balls tend to be positioned in the internal recess provided in the cylindrical member, and when the balls abut the inwardly-tapering portion of the knob, the balls tend to be positioned out of the internal recess provided in the cylindrical member.

20. A tissue punch for cutting a hole in tissue, said tissue punch comprising: a cylindrical tube having a cutter blade at its end; and a plunger movable along a first axis to rotate the cylindrical tube about a second axis, said first axis and said second axis being transverse to each other, further comprising a knob at an end of the tissue punch, said knob being received in a generally cylindrical member, said plunger mechanism further comprising a spring and a retaining assembly, one end of the spring contacting an external shoulder of the cylindrical member, another end of the spring contacting the retaining assembly.

21. A tissue punch as recited in claim 20, said retaining assembly comprising a retaining washer and a bushing, wherein the bushing abuts the cylindrical tube and receives an inside circumferential surface of the retaining washer, wherein an outside circumferential surface of the retaining washer is retained in an internal recess provided in the tissue punch.

* * * * *